United States Patent
DeSilva et al.

(10) Patent No.: US 9,927,325 B2
(45) Date of Patent: Mar. 27, 2018

(54) METHOD AND SYSTEM FOR DETERMINING DISTRIBUTION OF TEMPERATURE AND VELOCITY IN A GAS TURBINE ENGINE

(71) Applicant: Siemens Energy, Inc., Orlando, FL (US)

(72) Inventors: Upul P. DeSilva, Oviedo, FL (US); Heiko Claussen, North Brunswick, NJ (US)

(73) Assignee: SIEMENS ENERGY, INC., Orlando, FL (US)

( * ) Notice: Subject to any disclaimer, the term of this patent is extended or adjusted under 35 U.S.C. 154(b) by 356 days.

(21) Appl. No.: 14/844,078

(22) Filed: Sep. 3, 2015

(65) Prior Publication Data

US 2015/0377669 A1    Dec. 31, 2015

Related U.S. Application Data

(63) Continuation-in-part of application No. 14/341,924, filed on Jul. 28, 2014, now Pat. No. 9,752,959, which is a continuation-in-part of application No. 14/207,803, filed on Mar. 13, 2014, now Pat. No. 9,556,791.

(51) Int. Cl.
| | |
|---|---|
| *G01F 1/66* | (2006.01) |
| *G01M 15/14* | (2006.01) |
| *G01N 29/07* | (2006.01) |
| *G01N 29/46* | (2006.01) |

(52) U.S. Cl.
CPC ............ *G01M 15/14* (2013.01); *G01F 1/662* (2013.01); *G01N 29/07* (2013.01); *G01N 29/46* (2013.01); *G01N 2291/02836* (2013.01); *G01N 2291/02881* (2013.01)

(58) Field of Classification Search
CPC ......... F05D 2270/303; F05D 2270/804; F05D 2270/806; G01M 15/14; G01K 7/42; G01F 25/007; G01F 1/667
USPC ........ 701/100; 702/45, 48, 50, 54, 130, 142, 702/176; 374/141, 117–119, 120, 45, 374/147, 144; 73/861.18–861.31, 73/204.11–204.27
See application file for complete search history.

(56) References Cited

U.S. PATENT DOCUMENTS

| | | | | |
|---|---|---|---|---|
| 4,015,470 A | * | 4/1977 | Morrison .................. | G01F 1/66 73/32 A |
| 4,596,133 A | * | 6/1986 | Smalling ................. | G01F 1/662 73/24.01 |

(Continued)

*Primary Examiner* — William H Rodriguez

(57) ABSTRACT

Techniques for determining temperature and velocity in a space inside a gas turbine engine (100) include mounting acoustic sensors (150) in the engine. The sensors are mounted to detect acoustic signals in a space (108) of fluid flow without extending into the space. A first sensor (350a) is displaced a first distance (351) from a different second sensor (350b) in a first direction parallel to fluid flow through the space. First and second signals are detected at the first and second sensors, respectively. A travel time difference between the first and the second sensors is determined by control system (170) module (180) based on the first and second signals. Velocity of fluid flow in the space is determined by the module based on the travel time difference. Temperature of fluid flow in the space is determined by the module based on either the first or the second signals or both.

17 Claims, 17 Drawing Sheets

(56) References Cited

U.S. PATENT DOCUMENTS

| | | | | |
|---|---|---|---|---|
| 4,754,650 A * | 7/1988 | Smalling | | G01F 1/662 73/861.28 |
| 4,856,321 A * | 8/1989 | Smalling | | G01F 1/662 73/40.5 A |
| 5,369,998 A * | 12/1994 | Sowerby | | G01F 1/66 73/861.04 |
| 5,918,281 A * | 6/1999 | Nabulsi | | G01F 1/10 73/597 |
| 6,487,916 B1 * | 12/2002 | Gomm | | G01F 1/667 73/861.27 |
| 6,494,105 B1 * | 12/2002 | Gallagher | | G01F 1/662 73/861.27 |
| 6,502,465 B1 * | 1/2003 | Vedapuri | | G01F 1/66 73/861.04 |
| 6,895,825 B1 * | 5/2005 | Barkhoudarian | | G01F 1/662 73/861.28 |
| 7,159,472 B1 * | 1/2007 | Hastings | | G01F 1/662 374/E11.01 |
| 7,853,433 B2 | 12/2010 | He et al. | | |
| 8,565,999 B2 | 10/2013 | Bunce et al. | | |
| 2002/0105999 A1 * | 8/2002 | Wallen | | G01K 11/24 374/117 |
| 2004/0194539 A1 * | 10/2004 | Gysling | | G01F 1/667 73/61.45 |
| 2005/0066744 A1 * | 3/2005 | Kupnik | | G01F 1/662 73/861.03 |
| 2006/0016243 A1 * | 1/2006 | Nevius | | G01F 1/66 73/1.16 |
| 2007/0151363 A1 * | 7/2007 | Ramsesh | | G01F 1/662 73/861.27 |
| 2008/0066557 A1 * | 3/2008 | Yoshida | | G01F 1/66 73/861.02 |
| 2010/0027006 A1 * | 2/2010 | Hertens | | G01F 1/667 356/335 |
| 2010/0288055 A1 * | 11/2010 | Mueller | | G01F 1/66 73/861.28 |
| 2011/0223037 A1 * | 9/2011 | Smith | | F04B 49/06 417/12 |
| 2012/0150413 A1 * | 6/2012 | Bunce | | F02C 9/28 701/100 |
| 2012/0204620 A1 * | 8/2012 | Straub, Jr. | | G01F 1/66 73/1.35 |
| 2014/0130606 A1 * | 5/2014 | Schwarz | | G01F 1/66 73/861.25 |
| 2014/0144156 A1 * | 5/2014 | Lang | | G01K 11/24 60/793 |
| 2014/0278200 A1 | 9/2014 | DeSilva | | |
| 2015/0168190 A1 * | 6/2015 | DeSilva | | G01M 15/14 60/734 |
| 2015/0168229 A1 | 6/2015 | DeSilva | | |
| 2015/0168230 A1 * | 6/2015 | DeSilva | | G01K 11/24 374/117 |
| 2015/0260557 A1 * | 9/2015 | DeSilva | | G01F 1/66 702/48 |
| 2015/0260611 A1 * | 9/2015 | DeSilva | | G01M 15/14 73/112.01 |
| 2015/0260612 A1 * | 9/2015 | DeSilva | | G01M 15/14 702/48 |
| 2015/0377691 A1 * | 12/2015 | Ceglia | | G01F 1/66 73/1.16 |
| 2016/0258798 A1 * | 9/2016 | Muhammad | | F02C 9/26 |
| 2017/0356303 A1 * | 12/2017 | Hodge | | F01D 21/003 |

* cited by examiner

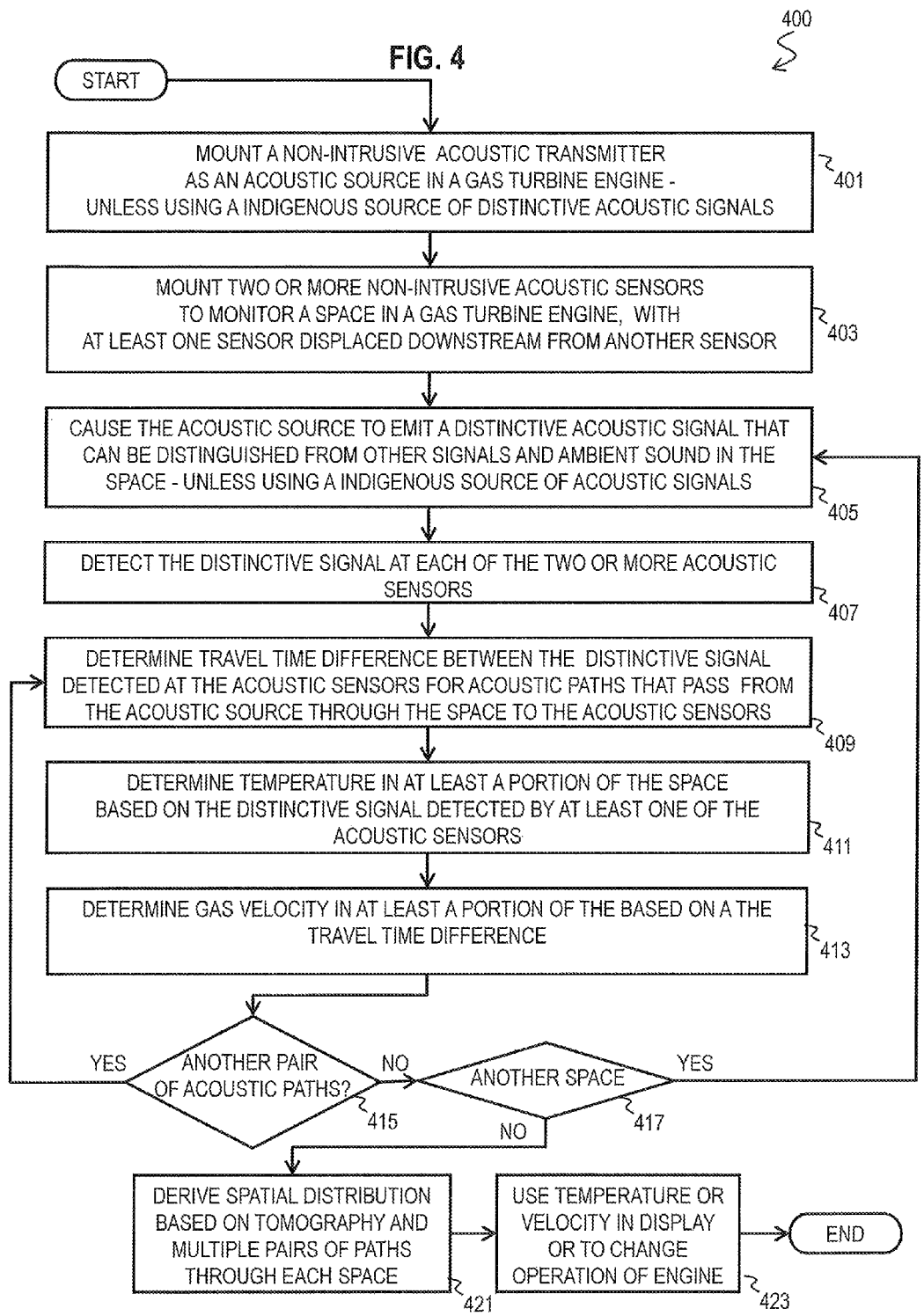

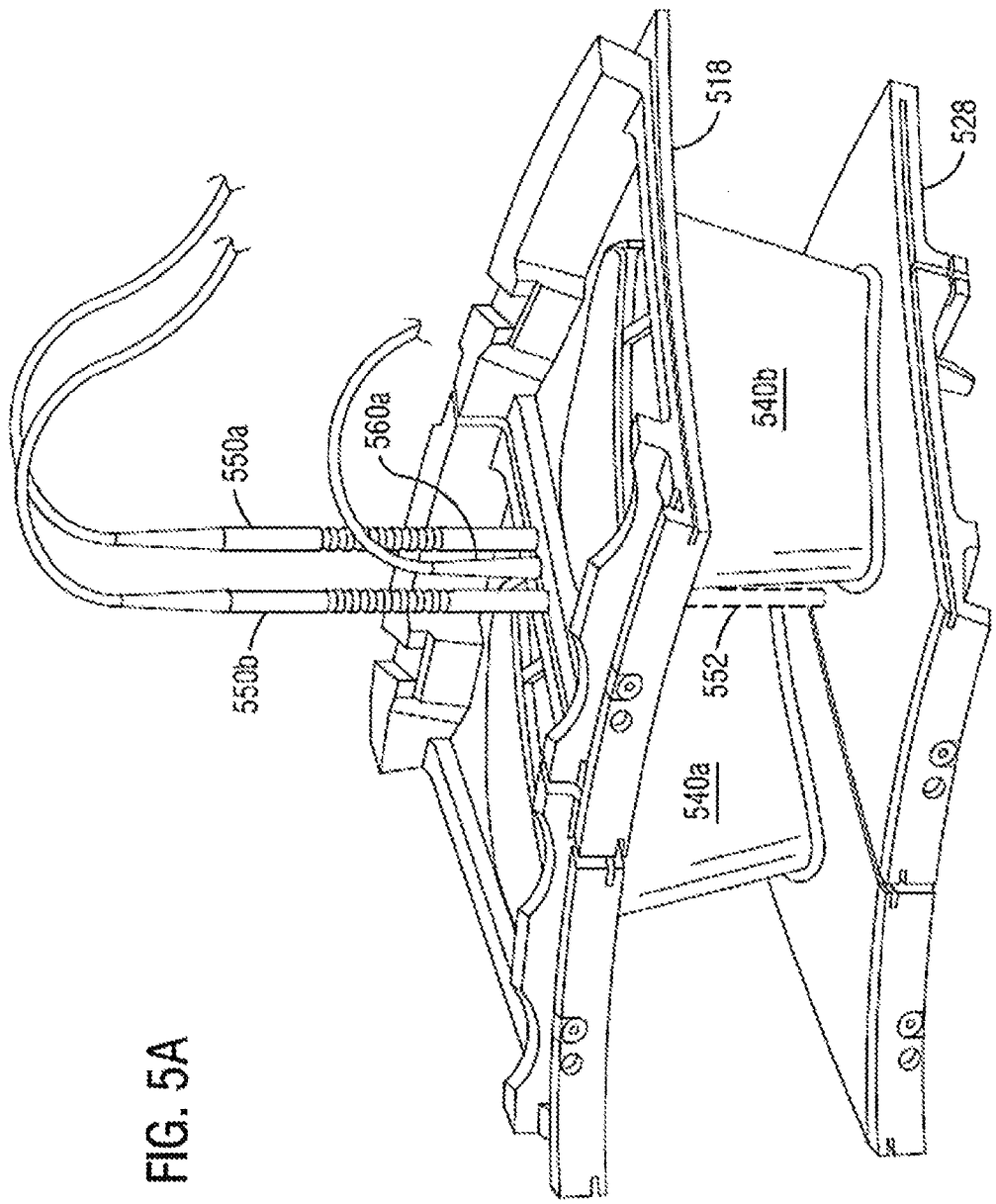

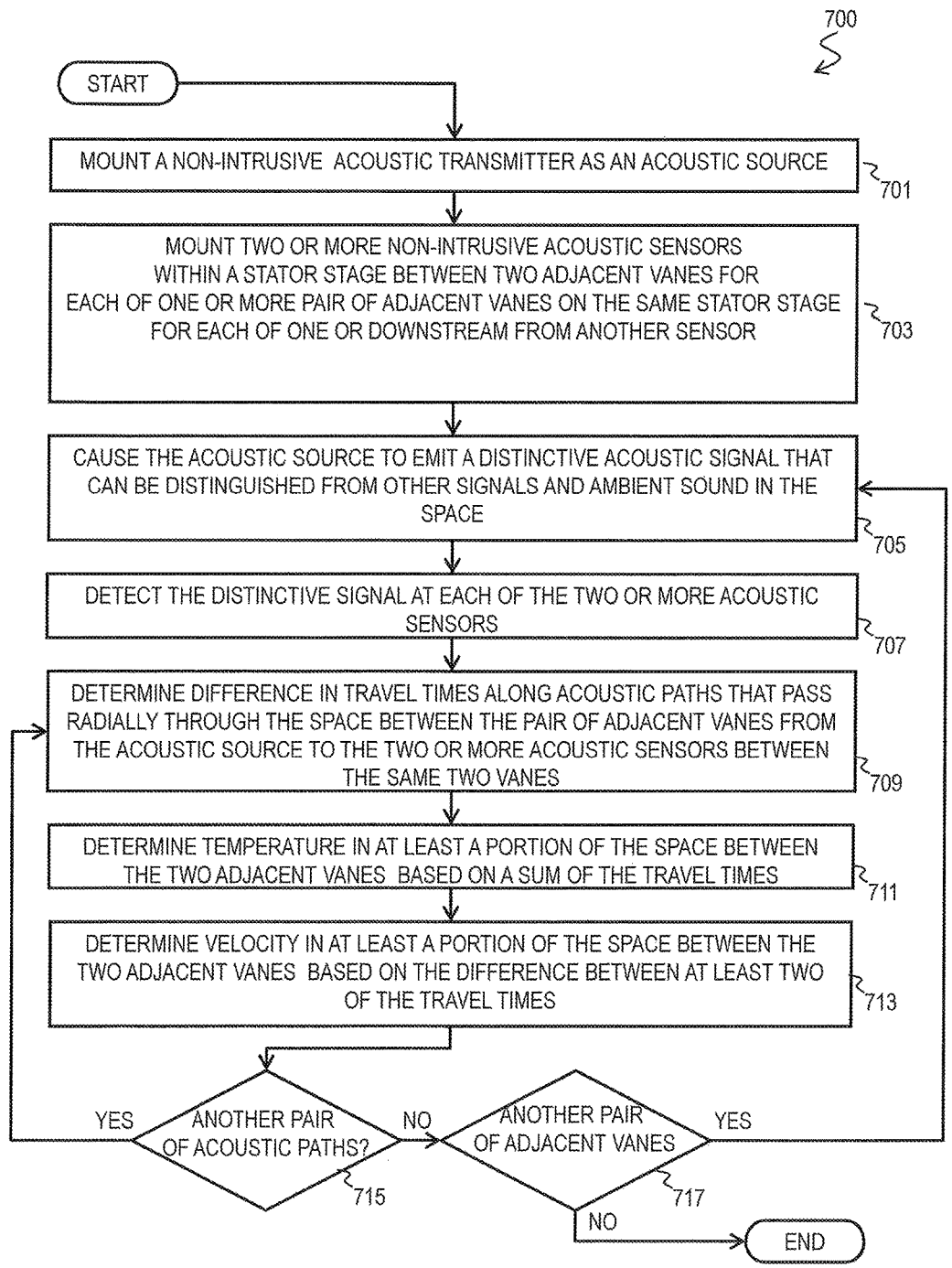

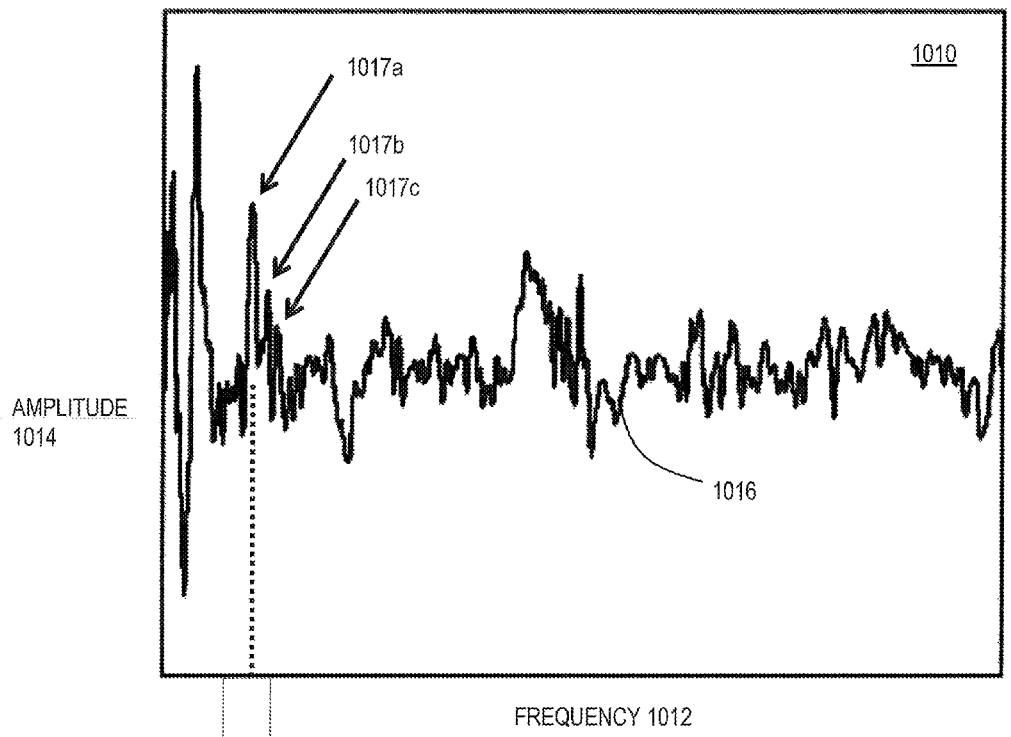
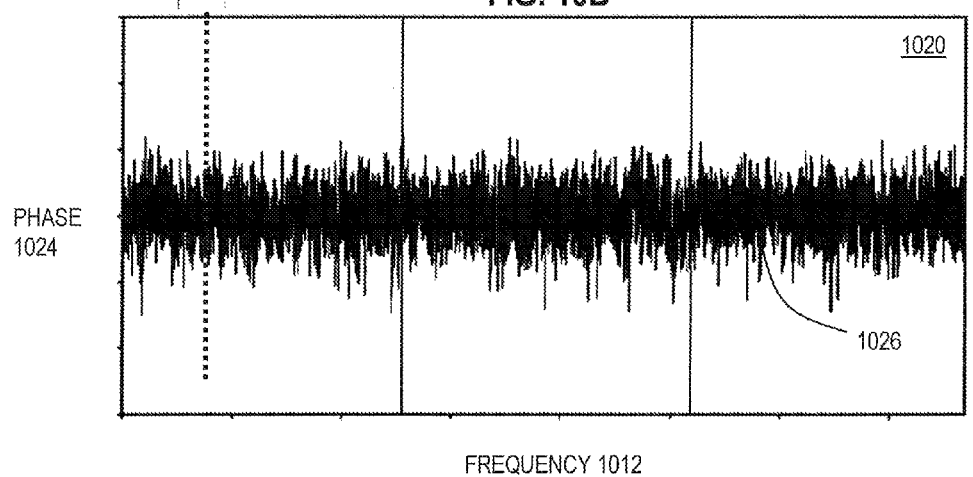

METHOD AND SYSTEM FOR DETERMINING DISTRIBUTION OF TEMPERATURE AND VELOCITY IN A GAS TURBINE ENGINE

CROSS-REFERENCE TO RELATED APPLICATIONS

This application claims benefit as a continuation-in-part of copending United States patent application entitled "Non-intrusive Transceiver and Method for Characterizing Temperature and Velocity Fields in a Gas Turbine Combustor," application Ser. No. 14/341,924, filed 28 Jul. 2014, which is a continuation-in-part of copending United States patent application entitled "Active Measurement of Gas Flow Velocity or Simultaneous Measurement of Velocity and Temperature, Including in Gas Turbine Combustors," application. Ser. No. 14/207,803, filed 13 Mar. 2014, the entire contents of each of which are hereby incorporated by reference as if fully set forth herein, under 35 U.S.C. § 120.

FIELD OF THE INVENTION

The various embodiments relate to determining the distribution of temperature and velocity in a gas turbine engine to assess real time design and operating characteristics of the engine.

BACKGROUND OF THE INVENTION

A gas turbine engine is a flow machine in which a pressurized gas expands. The gas turbine includes a turbine or expander, a compressor connected upstream of the turbine, and a combustion chamber between the compressor and turbine. Expanding gas produced in the combustion chamber drives blades of the turbine which provides power for the compressor and other engine output. The compression of air by way of the blading of one or more compressor stages subsequently mixes the compressed air in the combustion chamber with a gaseous or liquid fuel, where the mixtures is ignited by an ignitor to initiate combustion. The combustion results in a hot gas (mixture composed of combustion gas products and residual components of air) which expands in the following turbine section, with thermal energy being converted into mechanical energy in the process to drive an axial shaft. The shaft is connected to and drives the compressor. The shaft also drives a generator, a propeller or other rotating loads. In the case of a jet power plant, the thermal energy also accelerates a hot gas exhaust stream, which generates the jet thrust.

The gas turbine engine is designed to operate within certain ranges of pressure, velocity and temperatures of both the air and hot gas combustion products that vary with location through the engine. Optimal performance is achieved within very narrow ranges. Thus, to validate the design or to ensure that the gas turbine engine is operating within specified ranges or to make adjustments to attain the optimal performance, it is desirable to know the actual distribution of temperature, pressure and velocity during operation. Determining such distributions is challenging, at least in part, because the pressures and temperature can become very great.

Current approaches to monitoring the distribution of pressure, temperature and velocity in a gas turbine engine include some intrusive probes that project into the gas flows, including probes mounted on vanes (e.g., Kielhead probes) to obtain some profiles of velocity and temperature. Optical instruments have been used, but the characteristics of the optical devices can degrade at the extreme temperatures in at least portions of the turbine engine.

BRIEF DESCRIPTION OF THE DRAWINGS

Various embodiments of the invention are explained in the following description in view of the drawings that show:

FIG. 4 is a flow diagram that illustrates an example method for determining both velocity and temperature of gas flow in a gas turbine engine from the same two or more acoustic sensors and an indigenous or added acoustic source, according to an embodiment;

FIG. 5A and FIG. 5B are block diagrams that illustrate two views of example acoustic actuator and sensors relative to a space between two stator vanes, according to one embodiment;

FIG. 7 is a flow chart that illustrates an example method for using a known signal in a space between two stator vanes, according to an embodiment;

FIG. 10A and FIG. 10B are graphs that illustrate example spectral amplitudes of a signal from one sensor and spectral phases of two signals from different sensors for determining temperature and velocity of gas flow in a space, according to one embodiment;

DETAILED DESCRIPTION OF THE INVENTION

Figure 1A:
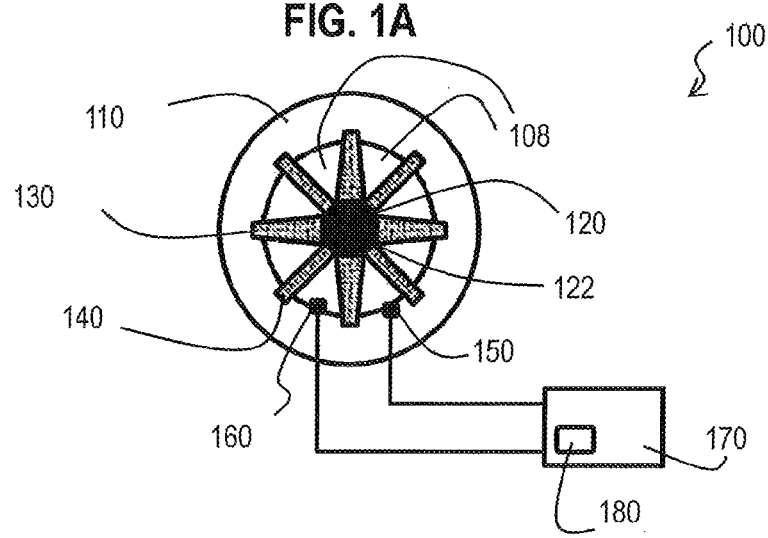
FIG. 1A is a block diagram that illustrates an example radial cross section of a gas turbine engine and control system, according to an embodiment.

It was recognized that intrusive probes can perturb the flow of air and hot gas in the engine and disrupt the very fields sought to be measured or optimized or both. It was further recognized that optical transducers, though capable of being deployed nonintrusively, suffer from narrow temperature ranges in which the transducers are effective, which inhibit operation at some temperatures achieved by gas flows in the gas turbine engine.

A method and apparatus are described for determining a distribution of temperature and velocity at spaces inside a gas turbine engine without the use of intrusive probes. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5X to 2X, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

As used herein a fluid is a material state that moves in response to a shearing stress, and includes both gas and liquid states of a material. In a gas turbine engine, the fluid is a gas comprising air, or an air and fuel mixture, or gases that result from combustion of air and fuel, or some combination.

FIG. 1A is a block diagram that illustrates an example radial cross section of a gas turbine engine and control system 100, according to an embodiment. This cross section includes a housing 110 symmetrically disposed around an axial shaft 122 that is perpendicular to the view of FIG. 1A. The shaft is part of a shaft assembly 120 that encloses the shaft and seals, at least partially, the gases inside the shaft assembly 120 from a main flow of air or other gas between the shaft assembly 120 and the housing 110. Fixed to the housing 110 and shaft assembly 120 are one or more stator stages of stator vanes 140. Each stator stage includes multiple stator vanes 140 spaced azimuthally around the shaft assembly 120. The stator vanes direct the main flow onto the rotor blades 130 in one or more rotor stages. Each rotor stage includes multiple rotor blades 130 spaced azimuthally around the shaft assembly 120 and displaced axially from a corresponding stator stage. Each rotor blade is connected to the axial shaft 122 and configured to rotate with the shaft 122 around an axis of rotation of the axial shaft, which runs along a length of the shaft, and thus is also perpendicular to the view of FIG. 1A.

Also included in this cross section is an acoustic actuator 160 (also called an acoustic transmitter) configured to introduce acoustic energy into the main gas flow (called simply gas flow hereinafter), and an acoustic sensor 150 (also called acoustic receiver) configured to detect acoustic energy from the gas flow. In some embodiments, there are multiple acoustic actuators 160 or acoustic sensors 150 or both. In some embodiments, either or both of one or more acoustic actuators 160 and acoustic sensors 150 are acoustic transducers that can both emit and detect acoustic signals.

Figure 11:
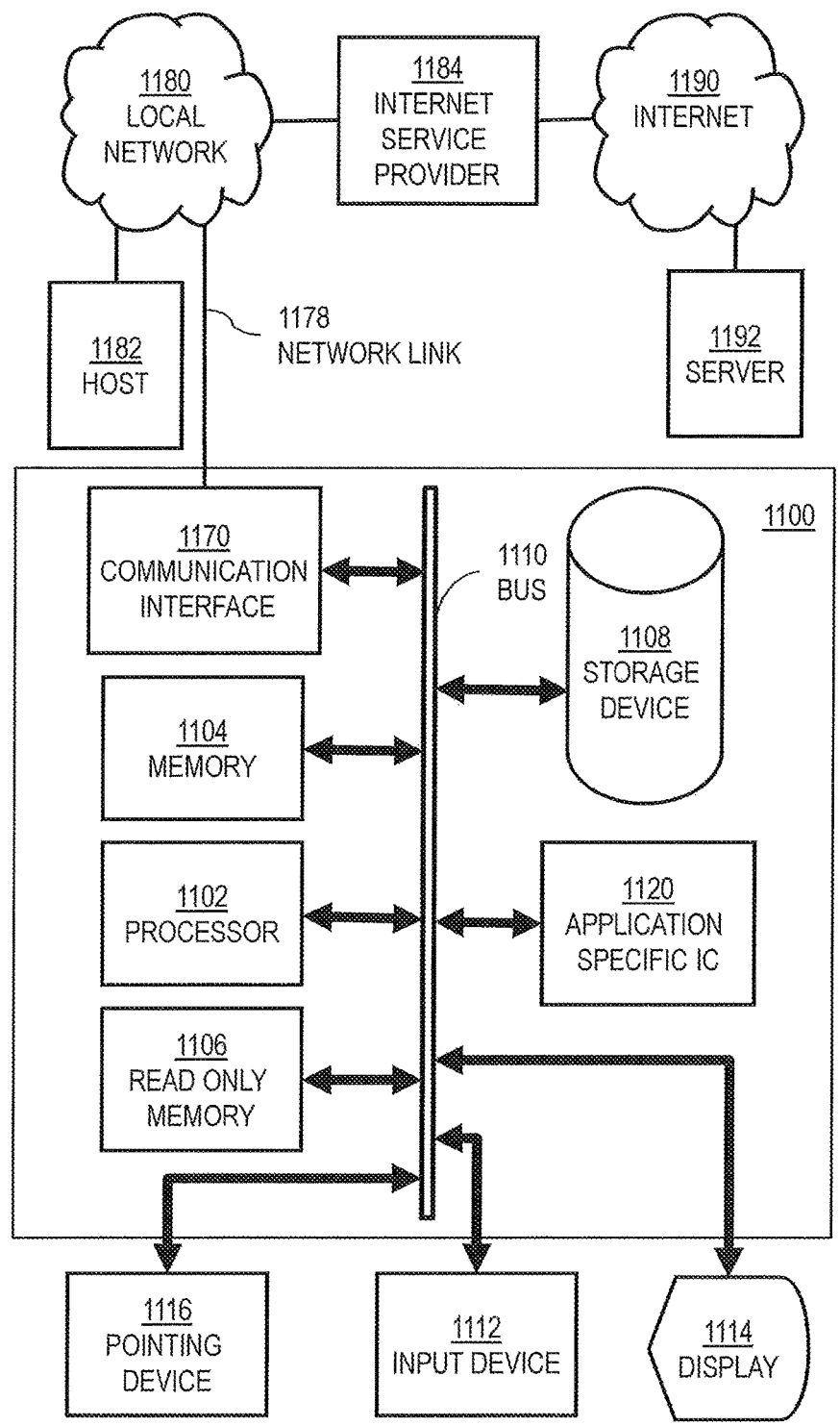
FIG. 11 is a block diagram that illustrates a computer system upon which an embodiment of the invention may be implemented.
Figure 12:
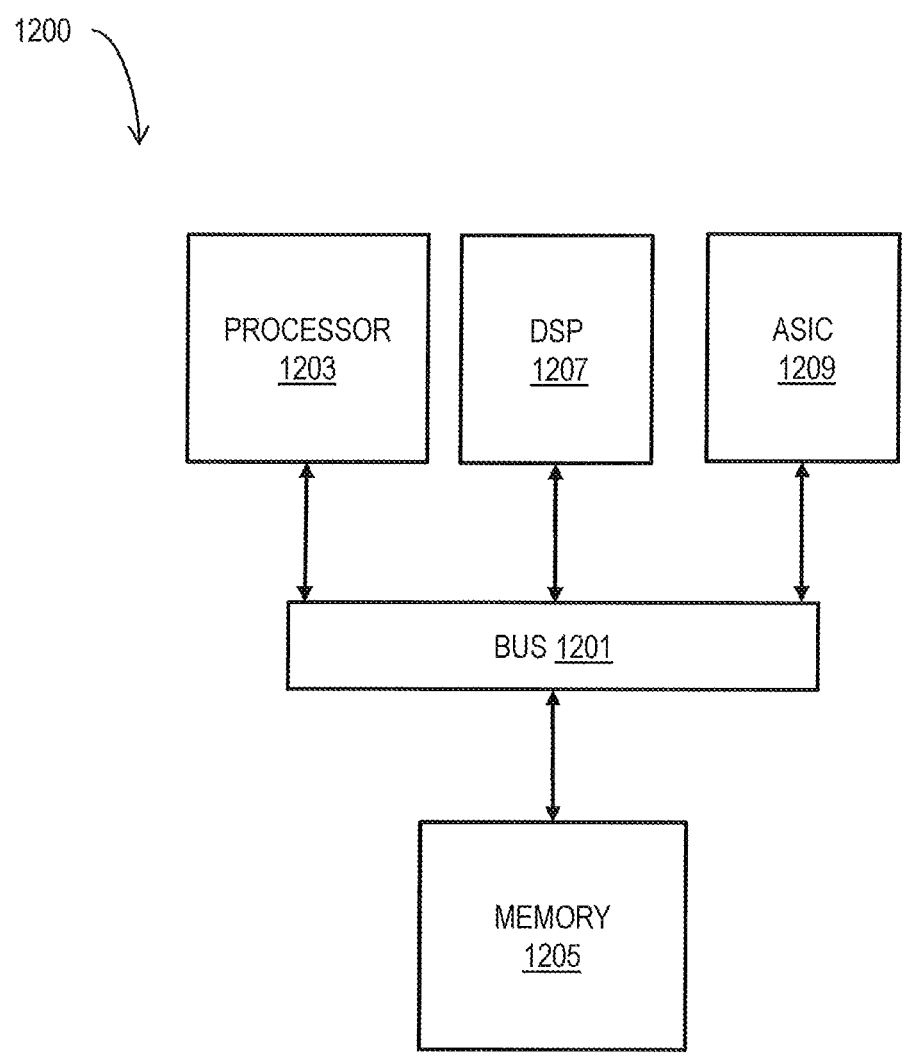
FIG. 12 is a block diagram that illustrates a chip set upon which an embodiment of the invention may be implemented.

The acoustic actuator is driven by electronic signals sent by control system 170 and electronic signals output from acoustic sensor 150 are collected and processed into acoustic data, or stored, or some combination, at the control system 170. The control system 170 includes a chip set as depicted in FIG. 12 or a computer system as depicted in FIG. 11, and as described in more detail below in reference to those figures. The lines connecting sensor 150 and actuator 160 to control system 170 indicate lines of electrical communication and may be wired or wireless. The control system includes a temperature/velocity detection module 180 configured to deduce the distribution of temperature and velocity in at least a portion of the main flow based on the data collected from the acoustic sensor 150. In some embodiments, the acoustic actuator 160 is omitted. In some embodiments, the acoustic actuator 160 is configured to place acoustic signals into the gas flow, using signals that are designed to assist in the determination of the distribution of temperature or velocity, or both, in the gas flow of the gas turbine engine 100 in the presence of other acoustic signals or in the presence of acoustic or electronic noise, or some combination.

Figure 1B:
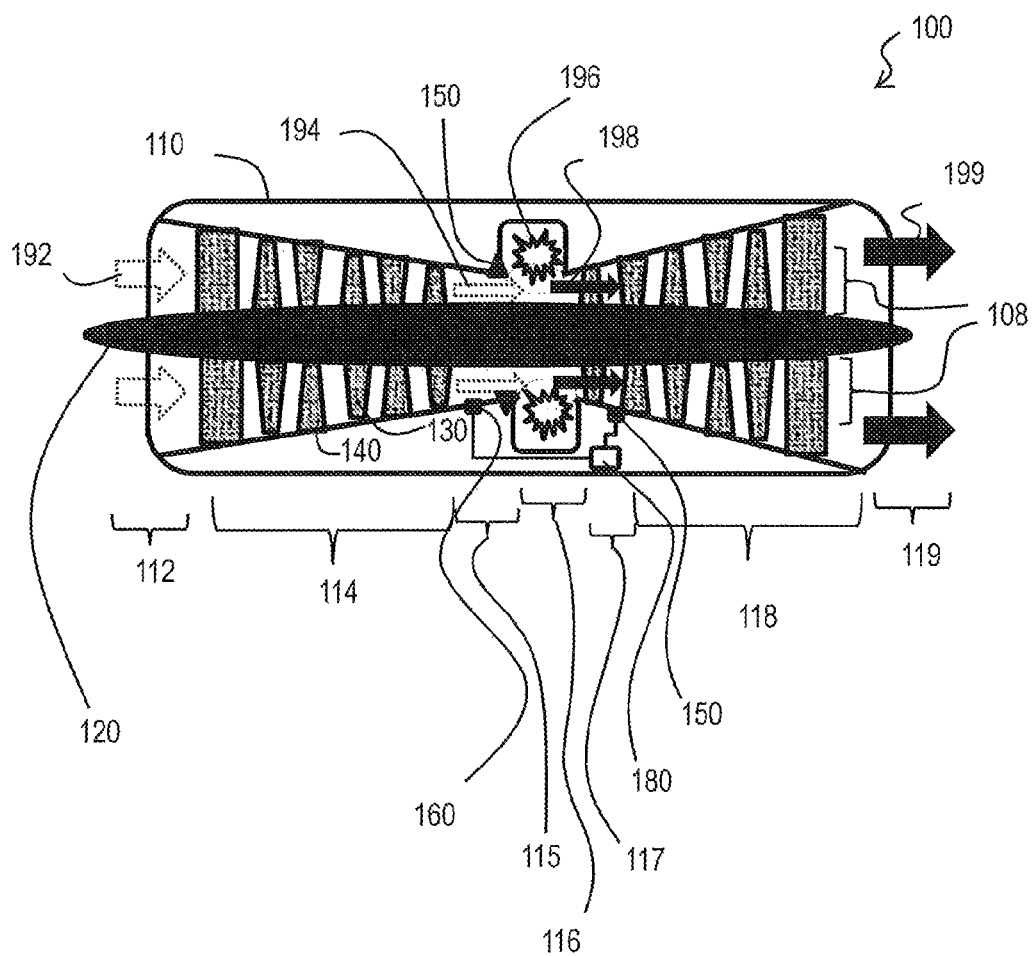
FIG. 1B is a block diagram that illustrates an example axial cross section of a gas turbine engine with components of a control system, according to an embodiment.

FIG. 1B is a block diagram that illustrates an example axial cross section of a gas turbine engine and control system 100, according to an embodiment. The system includes housing 110, shaft assembly 120, rotor blades 130, stator vanes 140, acoustic sensor 150, acoustic actuator 160 and temperature/velocity detection module 180 as defined above with reference to FIG. 1A. As can be seen in FIG. 1 B, along the axis the engine includes, in succession, an inlet section 112, a compressor section 114, a compressor diffuser section 115, a combustion section 116, a transition section 117, a turbine section 118, and an exhaust section 119. In some embodiments, one or more of these sections are omitted, but all gas turbine engines include a compressor section 114, a combustion section 116 and a turbine section 118.

The air inlet section 112 provides clean and unrestricted airflow, as intake air 192, to the engine. Clean and undisturbed inlet airflow extends engine life by preventing erosion, corrosion, and foreign object damage.

The compressor section 114 is responsible for providing the engine with all the air it needs in an efficient manner. In addition, it must supply this air at high static pressures. This is accomplished by the rotor blades 130 forcing air against the stator vanes 140 in each stage (for convenience, only three rotor stages and three stator stages are depicted in FIG. 1B). In addition, velocity of the main flow is increased by the narrowing space between housing 110 and shaft assembly 120.

Each stage incrementally boosts the pressure from the previous stage. A single compression stage consists of a stage of rotor blades (called a rotor) followed by a stage of stator vanes (called a stator). The rotor blades are attached to the rotating shaft, e.g., by a rotating disk within the shaft assembly. The rotation of the shaft is driven in the turbine section as described below. The stator vanes are attached to a stationary ring, e.g., on the housing 110 or shaft assembly 120, or both. The flow between the compressor blades is slightly divergent. Flow between compressor vanes is also divergent, but more so than for the blades. The divergent flow converts velocity from the narrowing cross section of the gas flow and from the rotor stage into static pressure.

Figure 1C:
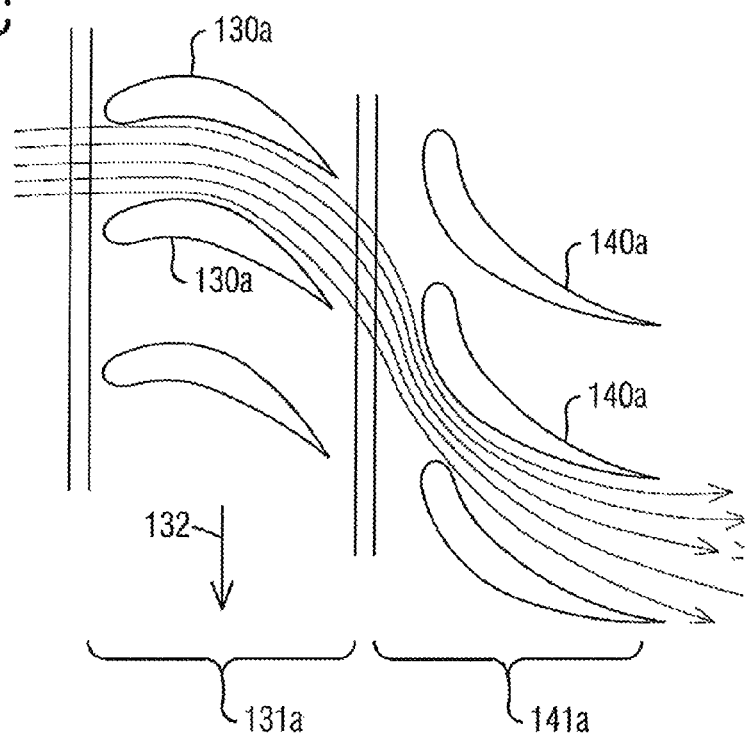
FIG. 1C and FIG. 1D are block diagrams that illustrate divergent and convergent fluid flows, respectively, induced by rotating blades and stator vanes in compressor and turbine sections, respectively, of the gas turbine engine of FIG. 1 B, according to an embodiment.
Figure 1D:
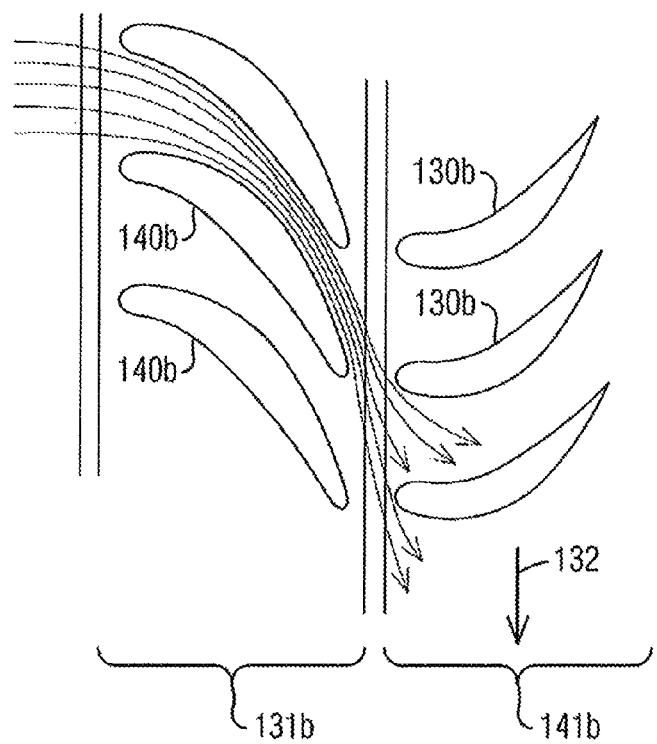

FIG. 1C and FIG. 1D are block diagrams that illustrate divergent and convergent fluid flows, respectively, induced by rotating rotor blades and fixed stator vanes in compressor and turbine sections, respectively, of the gas turbine engine of FIG. 1B, according to an embodiment.

In FIG. 1C a compressor stage is depicted, made up of a rotor blade stage followed by a stator vane stage. Each rotor blade 130 increases velocity (and the corresponding impact pressure, Pi), with a small increase in static pressure (Ps) due to the divergence of the blade flow path. The stator vanes slow the air by means of their divergent duct shape, converting the accelerated velocity (and associated impact pressure, Pi) to higher static pressure (Ps). The vanes are positioned at an angle such that the exiting air is directed into the rotor blades of the next stage at the most efficient angle. This process is repeated at each compression stage in the compression section 114.

For example, in a large turboprop, an axial flow compressor is assumed to contain fourteen stages each of rotor blades and corresponding stator vanes. The overall pressure ratio (pressure at the back of the compressor compared to pressure at the front of the compressor) is approximately 9.5:1. At 100% (>13,000 rotations per minute, RPM), the engine compresses approximately 12.3 cubic meters of air per second. At standard day air conditions, this equals approximately 15 kilograms (kg) of air per second. The compressor also raises the temperature of the air by about 300 degrees Celsius (° C.) as the air is compressed and moved rearward. The power required to drive a compressor of this size at maximum rated power is approximately 5000 kilowatts (kW, 1 kW=$10^3$ watts). The compressed air 194 output by the compressor is depicted in FIG. 1B.

In some embodiments, the compressor section also includes inlet guide vanes and the outlet guide vanes. These vanes, located at the inlet and the outlet of the compressor, are neither divergent nor convergent. The inlet guide vanes direct air to the first stage compressor blades at the "best" angle. The outlet guide vanes "straighten" the air to provide the combustor with the proper airflow direction. The efficiency of a compressor is primarily determined by the smoothness of the airflow.

Air has the natural tendency to flow toward low-pressure zones. If air were allowed to flow "backward" into the lower pressure zones, the efficiency of the compressor would decrease tremendously as the energy used to increase the pressure of the air would be wasted. To prevent this from occurring, seals are incorporated at the base of each row of vanes to prevent air leakage. In addition, the tip clearances of the rotating blades are also kept at a minimum by the use of coating on the inner surface of the compressor case.

During design, every effort is made to keep the air flowing smoothly through the compressor to minimize airflow losses due to friction and turbulence. This task is a difficult one, since the air is forced to flow into ever-higher pressure zones. Thus monitoring the velocity and temperature profile is important to both design and operation.

The compressor diffuser section 115 is a very divergent duct that converts most of the air's remaining velocity (impact pressure, Pi) into static pressure (Ps). As a result, the highest static pressure and lowest velocity in the entire engine is at the point of compressor diffuser section 115 discharge. Other aerodynamic design considerations that are important in the compressor diffuser section 115 include providing a short flow path, uniform flow distribution, and low drag loss.

Once the air flows out of the compressor diffuser section 115, it enters the combustion section 116, also called the combustor. The combustion section 116 has the difficult function of controlling the burning of large amounts of fuel and air. It must release the heat in a manner such that the air is expanded and accelerated to give a smooth and stable stream of uniformly heated gas at all starting and operating conditions. This function is desirably accomplished with minimum pressure loss and maximum heat release. In addition, combustion liners must position and control the fire to prevent flame contact with any metal parts that would be softened or melted in contact with the flame.

For example, six combustion liners (cans) are positioned at different azimuthal positions within an annulus created by inner and outer combustion cases adjacent the shaft assembly 120 and housing 110, respectively. Combustion takes place in the forward end or primary zone of the cans. Primary air (amounting to about one fourth of the total engine's total airflow) is used to support the combustion process. The remaining air, referred to as secondary or dilution air, is admitted into the liners in a controlled manner. The secondary air controls the flame pattern, cools the liner walls, dilutes the temperature of the core gasses, and provides mass. This cooling air is critical, as the flame temperature is above 1930° C. (3500 degrees Fahrenheit, ° F.), which is higher than the metals in the engine can endure. It is important that the fuel nozzles and combustion liners control the burning and mixing of fuel and air under all conditions to avoid excess temperatures reaching the turbine section or combustion cases. Maximum combustion section outlet temperature (turbine inlet temperature) in this example embodiment is about 1070° C. (>1950° F.) as depicted in FIG. 1B as combustion gasses 198.

In some embodiments, the rear third of the combustion liners is the transition section 117. The transition section 117 has a very convergent duct shape, which begins accelerating the gas stream and reducing the static pressure in preparation for entrance to the turbine section 118.

The turbine section 118 converts the energy of the expanding air/burned fuel gas mixture out of the combustor into mechanical energy to drive the shaft and thence the compressor, driven accessories, and, if present, a propeller. The expanding gas not used to generate mechanical energy leaves the exhaust section 119 providing forward thrust that is used, for example, in jet engines. The turbine section converts the energy of the hot gas into mechanical energy by expanding the hot, high-pressure gases to a lower temperature and pressure at each of several turbine stages (of which only three are depicted in FIG. 1B for convenience). Each turbine stage includes a stator stage of stator vanes followed by a rotor stage of rotor blades. This is the reverse of the order in the compressor. In the compressor, energy is added to the gas by the rotor blades, then converted to static pressure by the stator vanes. In the turbine, the stator vanes increase gas velocity, and then the rotor blades extract energy to rotate. The rotating rotor blades are connected to the shaft 122 to impart rotation to the shaft, e.g., by a rotating disk inside the shaft assembly.

As shown in FIG. 1D, the vanes and blades of each turbine stage are airfoils that provide for a smooth flow of the gases. As the main flow enters the turbine section from the combustion section, the flow is accelerated through the first turbine stage stator vanes. The stator vanes (also called nozzles) form convergent ducts that convert the heat and pressure of the gas into higher velocity gas flow (Pi). In addition to accelerating the gas, the vanes "turn" the flow to direct it into the rotor blades at an advantageous angle. As the mass of the high velocity gas flows across the turbine blades, the momentum of the gas is reduced and the work done converted to mechanical energy. Velocity, temperature, and pressure of the gas are sacrificed in order to rotate the rotors to generate shaft power. All the air should flow across the airfoils to achieve maximum efficiency in the turbine. In order to promote this, seals are used at the base of the vanes to minimize gas flow around the vanes instead of through the intended gas path. In some embodiments, the first few rotor stages of the turbine section 118 have tip shrouds to minimize gas flow around the tips of the rotor blades.

After the gases have passed through the turbine section 118, they are discharged through the exhaust section 119. Though some of the energy of the gas is converted to mechanical energy in the turbine section 118, a significant amount of power remains in the exhaust gases 199. This gas energy is accelerated through the convergent duct shape of the exhaust to make it more useful as jet thrust. The principle of equal and opposite reaction (Newton's third law of motion) means that the force of the exhausted air drives a vehicle forward.

Figure 2A:
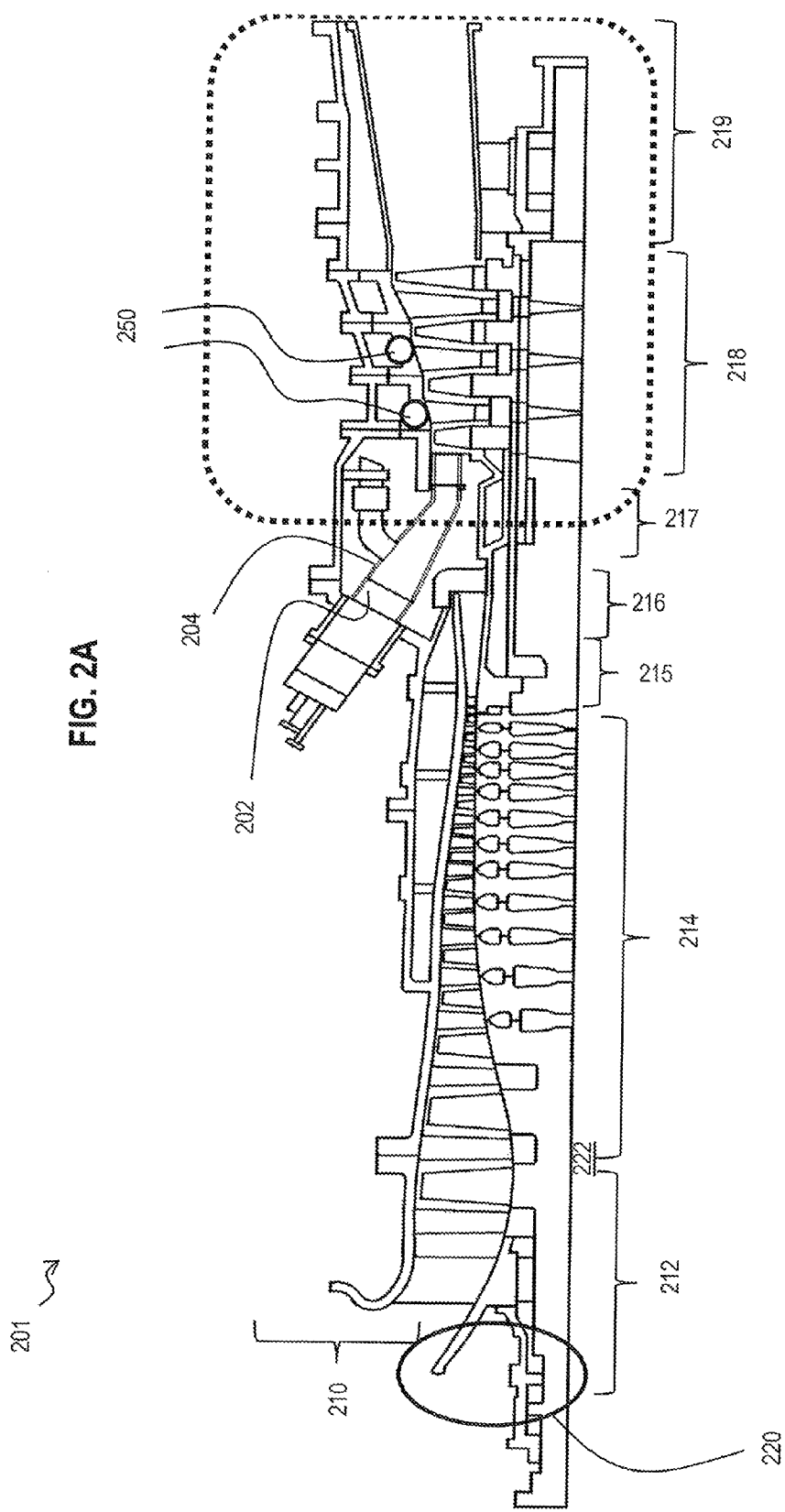
FIG. 2A and FIG. 2B are block diagrams that illustrate an upper half of a cross section of a gas turbine engine with example configuration of acoustic sensors; according to various embodiments.
Figure 2B:
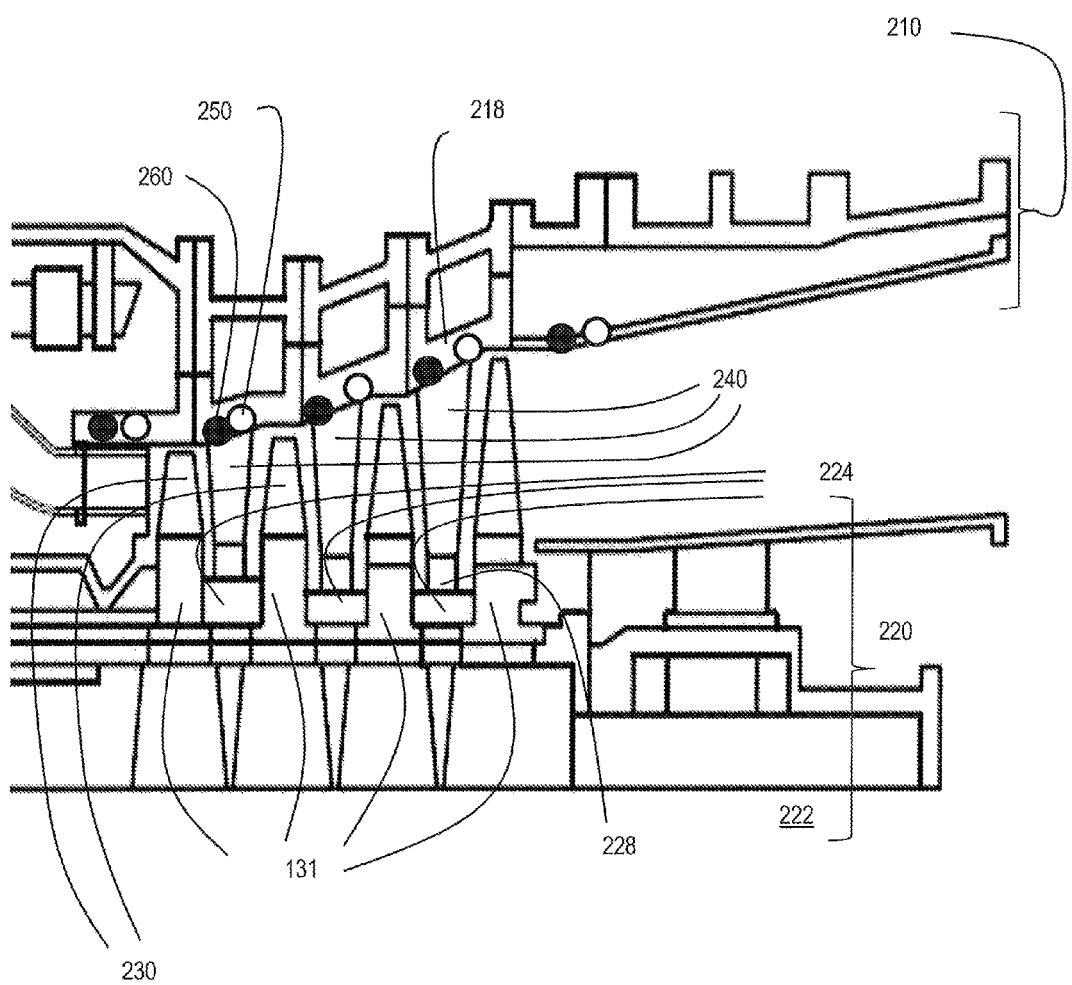

FIG. 2A and FIG. 2B are block diagrams that illustrate an upper half of a cross section of a gas turbine engine 201 with example configuration of acoustic sensors 250; according to various embodiments. The control system (such as control system 170) and communication lines thereto of a complete system for engine 201 are omitted for clarity. The portion of the cross section depicted is above an axial shaft 222, and includes an upper portion of a shaft assembly 220 and housing 210 separated by a gas flow space and multiple stages of rotors and stators in each of an inlet section 212, compressor section 214, diffusor section 115, combustion section 216, transition section 217, turbine section 218 and exhaust section 219, analogous to those sections described above. Also depicted is an ignitor 202 in the combustion section 216 and a combustion liner 204 (can) that extends from the combustion section 216 through the transition section 217 and discharges into the turbine section 218.

Note that at least two sensors 250 are included, one downstream of the other based on at least one spatial component of the direction of the gas flow, as described for one embodiment in more detail below with reference to FIG. 3A. According to various embodiments, two or more acoustic sensors are mounted to detect acoustic signals in a space of gas flow through the gas turbine engine without extending into the space. Thus, a first acoustic sensor is displaced a first distance from a different second acoustic sensor in a first direction parallel to a direction of fluid flow through the space. As depicted, at least one component of gas flow in in the axial direction from left to right in FIG. 2A, and thus at least one of the sensors 250 is displaced in the axial direction from the other one of the sensors 250. In other embodiments, such as in some embodiments described in more detail below, the sensors are disposed in different sections of a gas turbine engine than depicted with sensors 250 in FIG. 2A.

In one embodiment, the sections outlined by a dotted curve in FIG. 2A are populated with two or more sensors 250 and zero or more actuators. While acoustic actuators (transmitters) and sensors (receivers) are distinguished in embodiments depicted in FIG. 2A and FIG. 2B among other drawings to follow, it is understood that in alternative embodiments one or more are each replaced by an acoustic transducer called a transceiver that can function as both an acoustic sensor and an acoustic actuator at the same time or at different times.

In the sections indicated by dotted line in FIG. 2A, FIG. 2B depicts the housing 210, and the shaft assembly 220 that includes the axial shaft 222 and four rotors 131 separated by three cavities 224. Rotor blades 230 extend outside the shaft assembly 220 and displace the gas flow spaces. The stator vanes 240 are attached to the housing 210 at stator space outer walls 218 farthest from the shaft and its axis of rotation, and attached to the shaft assembly at stator space inner walls 228 closest to the shaft and its axis of rotation.

One or more acoustic sensors 250 (represented by open circles) are mounted between adjacent stator vanes of a single stator without intruding into that space between those two adjacent stator vanes (such as being mounted in outer wall 218 or inner wall 228 or in stator vane 240), for each of one or more pair of adjacent stator vanes on one stator stage, for each of one or more stator stages in each of one or more sections of the gas turbine engine 201. In these various embodiments, zero or more acoustic actuators 260 (represented by filled circles) driven by a control system (such as control system 170) are also included for each space between adjacent stator vanes without intruding into the space. Multiple sensors can detect signals originating from each acoustic source, such as the actuators 360, so that profiles of temperature and velocity can be obtained by combining information from each unique combination of acoustic source and acoustic sensor. In some embodiments, passive acoustic sources not driven by a control system (such as control system 170) are used in addition to or instead of the acoustic actuators (160, 260) that are driven by the control system. As used herein, an acoustic source refers to either an acoustic actuator driven by a control system or a passive source, or some combination. Example passive sources include cavities 224 that resonate at different acoustic frequencies at different temperatures. Some such embodiments are described in more detail below with reference to FIG. 9A through FIG. 10B.

In the illustrated embodiment, one acoustic actuator 260 and one acoustic sensor 250 are mounted to detect acoustic signals in a space between one pair of adjacent stator vanes on each of four stator stages located only in a transition section 217 and turbine section 218. It is advantageous to locate those actuators and sensors in these sections because here the temperatures and speeds of the gas flow are higher and more informative about the performance of the engine than other sections for many design and operational purposes. Also in these locations the temperatures vary enough to obtain useful variations in resonance frequencies of the cavities 224.

Figure 3A:
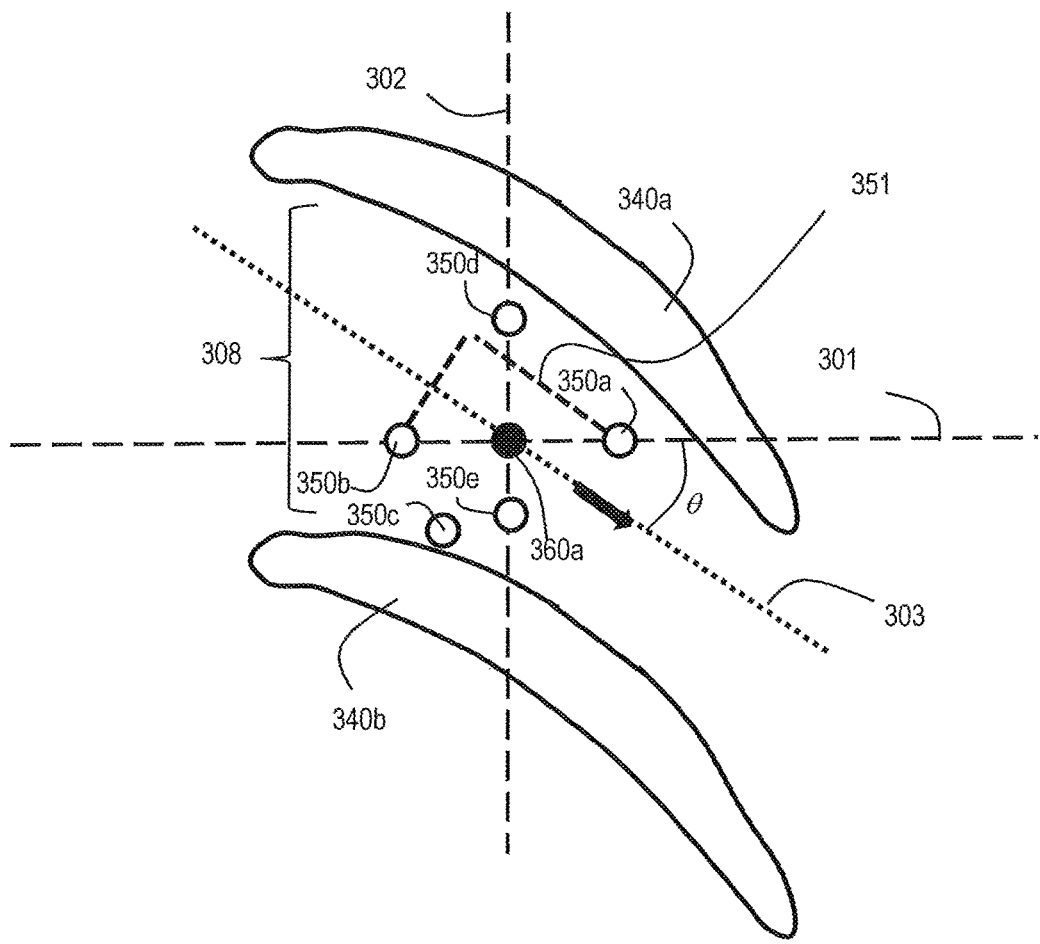
FIG. 3A and FIG. 3B are block diagrams that illustrate an example configuration of acoustic sensors relative to an acoustic actuator for a space between two vanes on a single stator; according to various embodiments.
Figure 3B:
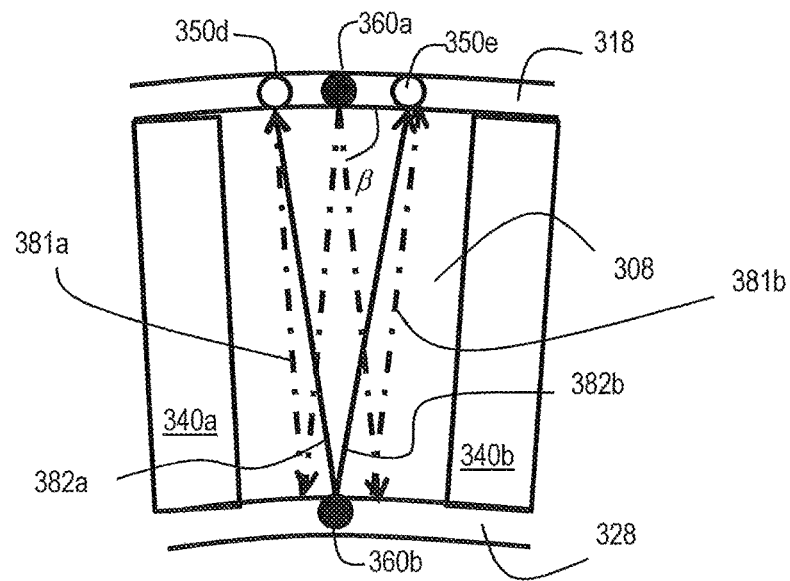

FIG. 3A and FIG. 3B are block diagrams that illustrate an example configuration of acoustic sensors relative to an acoustic actuator for a space between two vanes on a single stator; according to various embodiments. FIG. 3A depicts a view from above toward the axial shaft in a gas flow space 308 between two adjacent stator vanes 340a and 340b (collectively referenced hereinafter as vanes 340). Two planes perpendicular to the view intersect FIG. 3A along dotted lines. An axial plane 301 includes the axis of rotation of the axial shaft; and, a radial plane 302 is perpendicular to the axis of rotation. Movement up and down in the radial plane at constant radius, as from one vane to the next, is the azimuthal direction. Gas flow between the vanes 340 is in flow direction 303 at angle θ, and the speed of the flow is represented by the length of the solid arrow. The velocity of the gas flow, given by the speed and direction 303, includes a downstream component to the right along this view of the axial plane and an azimuthal component down along this view of the radial plane. Similarly, distances in this plane have a component parallel to the direction of flow and a component perpendicular. For example, the distance from sensor 350a to sensor 350b includes a component Dab|| 351 that is parallel to θ, the direction of flow 303.

In the illustrated embodiment, an acoustic source 360a, such as an acoustic actuator or transceiver or passive source, is located between the adjacent vanes 340 on the radial plane 302, e.g., midway between the vanes 340, but in a manner not to intrude into the space with the gas flow. For example, the acoustic source 360a is located in an outer wall of the space 308.

In this embodiment, multiple positions for one or more acoustic sensors are indicated as sensors 350a, 350b, 350c, 350d, and 350e (collectively referenced hereinafter as sensors 350). Each is disposed to detect acoustic signals in the space 308, but also disposed so as to not intrude into the space; for example, each is disposed in an outer or inner wall of the space or in a stator vane.

Travel time from acoustic source to acoustic sensor depends on path length through the gas flow from source to sensor and on the speed of sound in the gas along the path and on gas flow velocity along the path. To distinguish the effect of sound speed from the effect of gas flow velocity in the measurements of travel time or travel time difference, at least two independent measurements are made of detected acoustic signals, each measurement based on a different acoustic sensor. Thus at least two acoustic sensors (or transceivers) are disposed to make independent measurements that can be mathematically processed to separate sound speed from gas flow velocity. Furthermore, sound speed depends on temperature of the gas, thus the measurements of gas sound speed also provide gas flow temperature. By combining measurements from multiple nonintrusive acoustic sources and nonintrusive acoustic sensors, profiles of gas flow temperature and gas flow velocity can be made in a gas turbine engine, without interfering with the flow of gas through the engine.

It is advantageous to place two transceivers (sensor and source in one) on the flow direction line and as far apart as possible while still being between the vanes. This way the measurement paths are maximally similar for upstream and downstream and the signals are maximally affected by the flow thus giving maximum sensitivity and accuracy.

Sound speed in a gas can be determined from travel time along a path that is not affected by gas flow, such as a path that is always perpendicular to the direction of gas flow, or by an indirect measurement of temperature. Both approaches are taken in various embodiments described below. In one embodiment illustrated in FIG. 3A, sensor 350c is displaced from acoustic source 360a in a direction perpendicular to the flow direction 303. A path through the space from source 360a to sensor 350c, should be dependent only on sound speed and not on gas flow velocity, and the travel time along this path can be used to deduce average sound speed along the path and therefore average temperature along the path. The dependence of sound speed on temperature is known for several gas mixtures found in gas turbine engines. For a determined or known composition of the gas, it is possible to determine the temperature of the gas based on the measured time for an acoustic or sound signal to travel the distance between the source 360 and sensor, e.g., sensor 350c, based on the speed of the sound signal traveling through the gas. The temperature, T (in degrees Celsius, ° C.), of the gas may be calculated using Equation 1a.

$$T = \{d/(B*t)\}^2 - 273.16 \quad (1a)$$

where d is the distance of the path traveled by the acoustic signal from source to receiver, t is the time-of-flight for the acoustic signal to travel along the path (the ratio d/t is the sound speed Ss of the gas near the sensors), and B is the acoustic constant given by Equation 1b.

$$B = \sqrt{\{(\gamma * R)/M\}} \quad (1b)$$

where γ is the ratio of specific heats of the gas, R is the universal gas constant (8.314 Joules per mole and per degree Kelvin, J/mole°K) and M is the molecular weight of the gas in kilograms per mole, kg/mole.

To determine the effects of gas flow velocity, at least one sensor is displaced from the source 360a in a direction of a velocity component of gas flow. The travel time is along the path connecting the source and the sensor is given by the distance ds traveled to the sensor, and the net speed of propagation, which is the sum of the average speed of sound Ss along the path (a function of temperature as given by Equation 1a) and the average Vpath, which is the component of the velocity Vs of the gas flow along the path from source to sensor that is along the path.

$$ts = ds/(Ss + V\text{path}) \quad (2)$$

As shown below, this displacement is used to derive the component of gas flow speed in the direction of displacement. For example, sensor 350a is downstream in the axial direction and sensor 350b is upstream in the axial direction and either or both can be used to determine the component of the flow in that direction. Similarly, sensor 350e is downstream in the azimuthal direction and sensor 350b is upstream in the azimuthal direction and either or both can be used to determine the component of the flow in the azimuthal direction. In addition, if the angle θ of flow direction 303 is known, then measuring the component of velocity in either direction allows the velocity to be determined, as given by Equations 3a through 3d. By definition $$\tan(\theta) = Vr/Va \quad (3a)$$

$$\cos(\theta) = Va/V \quad (3b)$$

Where Va is the gas velocity component in the axial direction, Vr is the gas velocity component in the radial plane (azimuthal) direction, and V is the gas velocity (net speed in direction θ). Assuming for purposes of illustration that Va is determined from the measurements to be described below, then Vr and V can be determined as given by Equations 3c and 3d.

$$Vr = Va \tan(\theta) \quad (3c)$$

$$V = Va/\cos(\theta) \quad (3d)$$

In general, for a flow direction at a known angle α in the plane of FIG. 3A from a direction between a source and sensor, with measured gas flow velocity Vs, the perpendicular component Vp and net velocity V can be determined as given by Equation 4a and 4b.

$$Vp = Vs \tan(\alpha) \qquad (4a)$$

$$V = Vs/\cos(\alpha) \qquad (4b)$$

Thus for known gas flow temperature, and therefore known sounds speed Ss, any combination of one source and one sensor, or two transceivers, that are at an angle a not perpendicular to the flow direction θ (e.g., not spaced apart within a few degrees of a direction of θ=+/−90 degrees) can be used to detect directly one component of the velocity and hence, with known value for α, determine the total velocity V. Stated another way, a first acoustic sensor (e.g., 350a) of the plurality of acoustic sensors is displaced a first distance (e.g., Dab∥ 351) from a different second acoustic sensor (e.g., 350b) of the plurality of acoustic sensors in a first direction parallel to a direction (e.g., θ) of fluid flow through the space. Of course, if the sensor is along the flow direction 303 from the source, then α=0 and, as a consequence, V=Vs and Vp=0. If perpendicular to the flow, then α=90 degrees and the calculation of V involves a divide by zero and therefore the value is unknown.

FIG. 3B depicts a view of the radial plane 302 from the direction of the inlet section toward the direction of the exhaust section, showing the gas flow space 308 between the same two adjacent stator vanes 340a and 340b. This view demonstrates that the sensors 350 are disposed within the stator outer wall 318 of space 308 to avoid intruding into the space 308, yet disposed to be responsive to acoustic signals in the space 308. In other embodiments, one or more sensors 350 are in the stator inner wall 328 of the space 308, or in either or both vanes 340. Mounting the sensors in the outer wall 318 offers the advantage of simplifying a wired connection to the control system 170. Embodiments in which the sensors 350 are mounted in the vanes 340 or inner wall 328 can involve extra complexity or cost or both, e.g., by extending wires from the outer wall 318 through the vanes 340 or using wireless sensors or some combination.

Figure 5B:
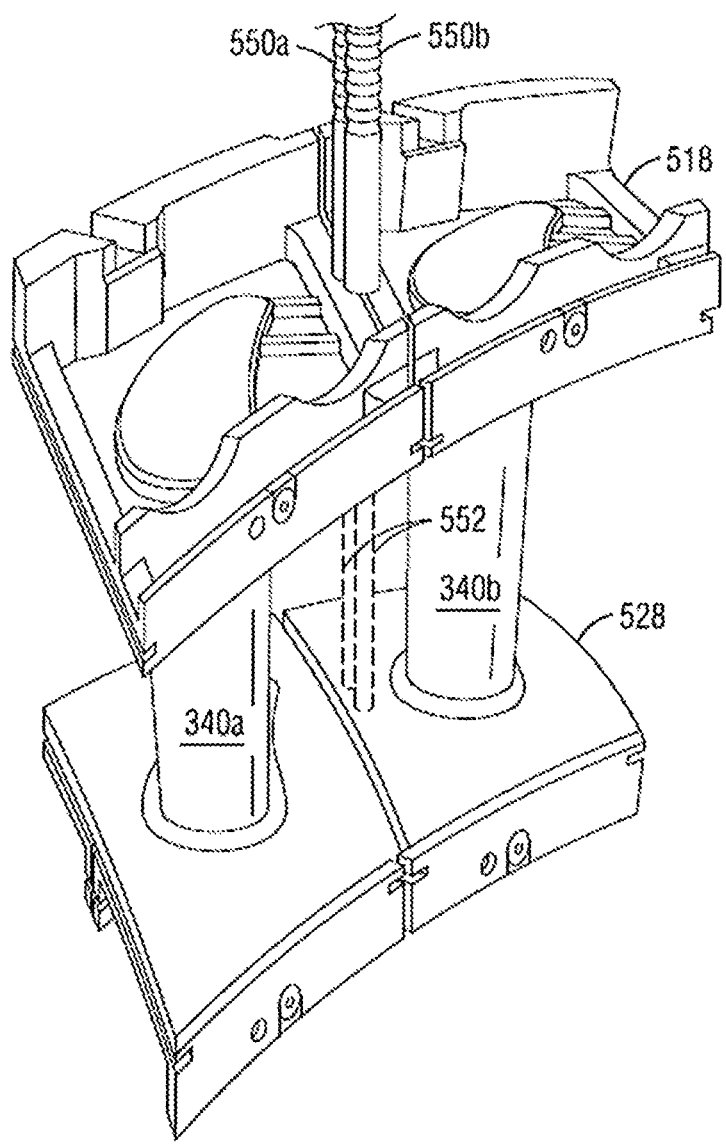

Similarly, an acoustic source may be disposed in either the stator outer wall 318, such as acoustic source 360a (and described in more detail in an embodiment represented by FIG. 5A and FIG. 5B), or the stator space inner wall 328, such as acoustic source 360b, or either or both vanes 340. For example, a passive acoustic source arising in the cavities 224 can be used as an acoustic source 360b in or below the stator inner wall 328 (such as described in more detail below with reference to FIG. 9A).

FIG. 3B also shows example paths of interest for determining temperature and velocity in the gas flow that passes through space 308. For both source and sensor in the same wall, such as source 360a and sensors 350d and 350e, a direct path, not shown, from source to sensor would not travel far in the space 308 and would arrive quickly. To obtain a travel time that is affected by the gas temperature and velocity, it is desirable to use a path that traverses a radial extent of the space 308. Two example reflected paths that have the desired property include path 381a from source 360a to stator inner wall 328 to sensor 350d, and path 381b from source 360a to stator inner wall 328 to sensor 350e. These paths can be distinguished from the direct path, not shown, by being the second arrival at each sensor of the acoustic signal emitted by the source 360a. In some embodiments, the acoustic source 360 emits a narrow beam directed to the inner wall 328 that excludes the direct path. In some embodiments, the sensors 350 are configured with a narrow acceptance angle to exclude the direct path. In some embodiments, both the source and the sensors use narrow beams to avoid the direct path. In another embodiment, a source is disposed in an opposite wall, e.g., source 360b in the stator inner wall 328 is used so that the direct paths 382a and 382b to the sensors 350d and 350e in the outer wall 318, respectively, pass through the space 308.

While Vpath=Vs when the path is parallel to the upper and lower walls, like the gas flow, when the path is directed at an acute vertical angle β relative to parallel flow of the gas, as depicted in FIG. 3B, the gas velocity component along the path is given by Equation 4c.

$$V\text{path} = Vs\cos(\beta) = V\cos(\alpha)*\cos(\beta) \qquad (4c)$$

Note that the tan(β) is equal to twice the radial height of the space 308 divided by the distance between the sensors.

Using two measurements of travel time from one source to two sensors, the contributions of average V and average Ss can be sorted out even if there is no independent indication of temperature. The following equations are presented to illustrate some principles, but the invention is not limited by the accuracy or completeness of these equations. In other embodiments, other approximations or numerical methods are used.

More generally, for speed of sound c(x,y,z) and velocity vector u(x,y,z) that are functions of three spatial coordinates, x, y, z, for $p_{AB}$ a unit vector in direction from acoustic transceiver A to acoustic transceiver B, for $t_{AB\ travel}$ time from A to B and $t_{BA}$ travel time from B to A, the integral equations 4d, 4e and 4f apply.

$$t_{AB} = \int_{A,B} \{c(x,y,z) + p_{AB} \cdot u(x,y,z)\}^{-1} ds \qquad (4d)$$

$$t_{BA} = \int_{B,A} \{c(x,y,z) - p_{AB} \cdot u(x,y,z)\}^{-1} ds \qquad (4e)$$

$$t_{AB} + t_{BA} \approx \int_{B,A} 2\{c(x,y,z)\}^{-1} ds \text{ if } \|c(x,y,z)\| \gg \|u(x,y,z)\| \qquad (4f)$$

For example, assuming there are travel time measurements ts1 and ts2 to two sensors separated from the acoustic source by a distance ds1 and ds2, respectively, along two paths at angles α1 and α2 from the direction of flow in the plane of FIG. 3A, and angles β1 and β2 from the direction of flow in a plane, like that of FIG. 3B, perpendicular to the plane of FIG. 3A, and that average sound speed Ss and average gas flow velocity V are the same over the two paths, then a system of equations given by 5a and 5b apply, simplifying the functional form of equations 4d and 4e.

$$ts1 = ds1/\{Ss + V\text{path}1\} = ds1/\{Ss + V\cos(\alpha1)\cos(\beta1)\} \qquad (5a)$$

where Vpath1 is component of gas flow along path 1, $$ts2 = ds2/\{Ss + V\text{path}2\} = ds2/\{Ss + V\cos(\alpha2)\cos(\beta2)\} \qquad (5a)$$

and Vpath2 is the component of gas flow along path 2. The pair of equations can be rewritten as $$Ss + V\cos(\alpha1)\cos(\beta1) = ds1/ts1 \qquad (5c)$$

$$Ss + V\cos(\alpha2)\cos(\beta2) = ds2/ts2 \qquad (5d)$$

Subtracting Equation 5d from Equation 5c eliminates Ss to get an equation for the average velocity, V, over the two paths in terms of known quantities ds1, ds2, α1, α2, β1, β2 and measured quantities ts1 and ts2.

$$V = \{ds1/ts1 - ds2/ts2\}/\{\cos(\alpha1)\cos(\beta1) - \cos(\alpha2)\cos(\beta2)\} = \{ds1*ts2 - ds2*ts1\}/[ts1*ts2\{\cos(\alpha1)\cos(\beta1) - \cos(\alpha2)\cos(\beta2)\}] \qquad (6a)$$

The value determined for V can be substituted into either Equation 5c or 5d or the sum to get a value for the average sound speed Ss over both paths. Using the sum gives Equation 6b.

$$Ss=\tfrac{1}{2}[ds1/ts1+ds2/ts2-V\{\cos(\alpha 1)\cos(\beta 1)+\cos(\alpha 2)\cos(\beta 2)\}]=\tfrac{1}{2}[\{ds1*ts2+ds2*ts1\}/[ts1*ts2-V\{\cos(\alpha 1)\cos(\beta 1)+\cos(\alpha 2)\cos(\beta 2)\}]] \quad (6b)$$

This value of Ss can be used to replace the ratio d/t in Equation 1a to get the average temperature over the two paths. The V term is negligible if the inequality in Equation 4f applies, which is the usual case.

If both sensors are on the same line with the source but equidistant and in opposite directions, then ds1=ds2=ds, $\beta 1=\beta 2=\beta$, and $\alpha 1=\alpha 2+180$ (thus $\cos(\alpha 2)=-\cos(\alpha 1)$) so that Equation 6a and Equation 6b become Equation 6c and Equation 6d, respectively.

$$V=ds\{ts2-ts1\}/[ts1*ts*2\{\cos(\alpha 1)\cos(\beta 1)\}] \quad (6c)$$

$$Ss=ds\{ts2+ts1\}/[2*ts1*ts2] \quad (6d)$$

Note that gas velocity V is proportional to the difference in travel times. Note that in the Ss Equation 6d, the velocity terms cancel out and the sound speed is proportional to the sum of the travel times and independent of the gas velocity.

This determination can be used to provide average T and V values for one or two parameters of models for temperature and velocity profiles to deduce spatially changing values of temperature and velocity. Furthermore, in some embodiments, using multiple average values of temperature and velocity over multiple paths through the same space from multiple sources and sensors, profiles of temperature and velocity within the engine can be constructed using tomography techniques. Additional information on deriving temperature and salinity using models and inversion techniques are described in "Parameter Distribution Mapping in a Gas Turbine Engine," U.S. patent application Ser. No. 14/682,393, filed 9 Apr. 2015, incorporated herein by reference as if fully set forth herein.

If there is an independent indication of sound speed (e.g., based on travel time on a path perpendicular to the gas flow direction, or based on temperature, e.g., from an acoustic resonance frequency of a cavity 224 and inverting Equation 1a), then individual travel times ts1 and ts2 need not be determined. If a travel time difference can be inferred, e.g., from a phase difference in the upstream and downstream resonant frequencies, then Equation 5b can be subtracted from Equation 5a and rewritten as a quadratic equation in V with all coefficients having known values based on Ss, ds1, ds2, (ts2−ts1), $\alpha 1$, $\alpha 2$, $\beta 1$ and $\beta 2$. The quadratic equation can be solved using the quadratic formula. For example, with the assumptions of two symmetrically placed sensors, one upstream and one downstream of the resonant cavity, so the simplifying assumptions described above, ds1=ds2=ds, $\beta 1=\beta 2=\beta$, and $\alpha 1=\alpha 2+180$ (thus $\cos(\alpha 2)=-\cos(\alpha 1)$), also apply, then the gas velocity V is found using the quadratic formula for solving the quadratic equation of Equation 7.

$$0=V^2\{\cos^2(\alpha 1)\cos(\beta)(ts2-ts1)/ds\}+V\{2\cos(\alpha 1)\}-\{Ss^2\cos(\beta)(ts2-ts1)/ds\} \quad (7)$$

Note that the coefficients of Equation 7 include only the difference in travel times (ts2−ts1) and not the actual travel times individually. Note further that the coefficients do include the sound speed Ss (and, inherently, the corresponding temperature, T), so temperature or sound speed is provided independent of the travel time on paths affected by the gas velocity, such as on a path perpendicular to the direction of gas flow.

FIG. 4 is a flow diagram that illustrates an example method for determining both velocity and temperature of fluid flow using as an example gas flow in a gas turbine engine from the same two or more acoustic sensors and an indigenous or added acoustic source, according to an embodiment. Although steps are depicted in FIG. 4, and in subsequent flowchart FIG. 7, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 401 one or more acoustic transmitters, such as an acoustic actuator driven by a control system or a passive device such as a resonator stick, or some combination, is mounted in a gas turbine engine nonintrusively (i.e., without intruding into a space of gas flow for operation of the engine) as a corresponding number of acoustic sources to introduce distinctive acoustic signals into the space. In some embodiments, an indigenous acoustic source of distinctive acoustic signals in the space is used instead of the transmitter, and step 401 is omitted. In various embodiments, each transmitter can be mounted anywhere that enables the transmitter to introduce the distinctive acoustic signals into the space of any portion of the gas flow, including mounting the transmitter in the housing 110 or shaft assembly 120 or rotor blades or stator vanes of any of the sections 112, 114, 115, 116, 117, 118, 119 of the gas turbine engine. Any transmitter known in the art that can be mounted without intruding into the space of the gas flow, and that can withstand the temperatures in the spaces, can be used in various embodiments, alone or in any combination: for example, compressed air-driven horns, arc-driven transmitters similar to spark plugs, and cooled electrodynamic speakers such as in household audio speaker systems.

In step 403, two or more acoustic sensors are mounted in the gas turbine engine nonintrusively (i.e., without intruding into a space of gas flow for operation of the engine) to detect distinctive acoustic signals in the space. In various embodiments, each sensor can be mounted anywhere that enables the sensor to detect the distinctive acoustic signals in the space of any portion of the gas flow, including mounting the sensor in the housing 110 or shaft assembly 120 or rotor blades or stator vanes of any of the sections 112, 114, 115, 116, 117, 118, 119 of the gas turbine engine. In order to determine gas flow velocity, V, at least one of the sensors is displaced with a non-zero downstream component, e.g., displaced a first distance in a first direction parallel to a direction of fluid flow through the space. Any acoustic sensor known in the art, which can be mounted without intruding into the space of the gas flow, and can withstand the temperatures in the spaces, can be used in various embodiments, alone or in any combination. For example, capacitance-based microphones from BRUEL & KJAER™ of Norcross, Georgia (e.g., model 4191L); and fiber optics-based microphones from OXSENSIS™ of Didcot, Oxfordshire, England (e.g., model I-Phire200) and DAVIDSON™ of West Covina, Calif.

In step 405, the acoustic source, whether passive or driven by the control system 170, is caused to emit a distinctive acoustic signal that distinguishes that source from other sources and ordinary sounds of the gas turbine engine. Causing passive sources to emit involves operating the gas turbine engine so that the passive sources begin to emit acoustic signals in response to the operation of the gas engine, or causing other environmental changes that excite the source, or some combination. For acoustic actuators, the control system 170 sends electronic signals, either by wire or wirelessly, that cause the actuator to emit the distinctive acoustic signals. Any distinctive acoustic signals can be used, such as one or more distinctive acoustic frequencies at substantially elevated amplitudes compared to ordinary occurrence in gas turbine engines, in patterns of one or more pulses of the same or different durations or continuously. One or more sources for each of one or more spaces to be probed among the entire gas flow space of the entire engine is caused to emit, either in series or in parallel.

In step 407 the distinctive acoustic signal is detected at two or more sensors, along with other sounds generated by the gas turbine engine, and distinctive signals from a second or other acoustic sources, to produce a detected signal. Detected signals at two or more sensors are collected in step 407 by control system 170 to enable gas flow velocity V to be determined.

In step 409 travel time difference for one pair of acoustic paths from one source to two sensors is determined by module 180 for the next pair of acoustic paths among all the possible pairs of acoustic paths. In some embodiments, the travel time difference (e.g., ts2−ts1) is determined directly based on a phase difference between peaks of a given frequency, as described in more detail below with reference to FIG. 10A and FIG. 10B. In some embodiments, the travel times (e.g., ts1 and ts2) are determined as the time between the emission of the distinctive signal at the source and the time of arrival of that signal at the each of the two sensors. The travel time difference is then determined in step 409 by the module 180 by taking the difference of those two travel times.

In step 411, the temperature in at least a portion of the space is determined by module 180 based on the distinctive signal detected by at least one of the acoustic sensors. For example, in some embodiments, an average temperature of the space is determined based on the resonant frequency of one or more of the cavities 224 as detected at one or more of the sensors. The temperature of the cavity is determined from the detected acoustic frequency and dimensions of the cavity, as described in more detail below, and the temperature in the space is determined based on a known relationship between the temperature of the cavity and the temperature of the space, as determined, for example, in one or more calibration experiments. In some embodiments that obtain the travel times separately, the average sound speed along the two paths is determined from those travel times, e.g., using Equation 6d, and an average temperature is derived from that average sound speed and Equation 1a. In some embodiments, a profile of temperature in the space is deduced from the average temperature and a model of temperature spatial variations.

In step 413, the gas velocity, V, in at least a portion of the space is determined by module 180 based on a travel time difference. For example, in various embodiments, the gas velocity averaged over the pair of acoustic paths is determined using Equation 6a or Equation 6c or Equation 7. In some embodiments, a profile of temperature in the space is deduced from the average temperature and a model of gas velocity spatial variations.

In step 415, it is determined by the module 180 whether there is another pair of paths between a source and sensor for the same space. If so, control passes back to repeat steps 408, 411 and 413. If not, then control passes to step 417, in which it is determined by module 180 whether there is another space to probe with different acoustic sources or acoustic sensors or both. If so, control passes back to step 405 to cause the next acoustic source to emit. If not, then control passes to step 421. In some embodiments, step 421 is performed before step 417. In some embodiments, steps 705 and 707 are performed simultaneously by controller 170 for all acoustic paths or all spaces or some combination.

In step 421, a spatial distribution of temperature and velocity within the space is determined based on tomography (e.g., the inverse Radon transform, well known in the art) and multiple pairs of acoustic paths through the same space, e.g., for each of multiple different spaces within the gas turbine engine. In some embodiments, there is an insufficient number of pairs of acoustic paths through each space and step 421 is omitted.

In step 423 the speed and the temperature determined for the gas flow in the space is caused to be presented on a display or is caused to change operation of the gas turbine engine or both.

In the following, several specific embodiments are described in more detail. This next embodiment was based on a recognized need for measuring temperature and velocity (both bulk mean as well as spatial distribution) in front of each rotating stage of a turbine (or a compressor) for component and blade design validation as well as for engine performance assessment. This need is felt for both existing engine frames as well as new frames that are being designed for higher efficiency and lower emissions. Traditional intrusive probes of both temperature and velocity have been used in the form of thermocouple and pressure probes (either stand alone or arrays); but intrude and disrupt the very gas flow to be measured.

The illustrated embodiment utilizes installation of acoustic transmitters and receivers on each stage of stator vanes where the measurements of temperature and velocity are needed. The transmitters emit a specially designed series of acoustic signals across the gas path radially. The acoustic emitters and receivers are all installed on the top wall of the vane segment. This embodiment uses the reflection of the acoustic waves from the bottom surface and captures the reflected acoustic waves using the acoustic receivers that are mounted next to the transmitter. The minimum requirement of the acoustic sensors is one transmitter and two receivers. Alternatively, the minimum requirement is two transceivers (that are both source and receiver at the same time). This way, the acoustic path with the flow and against the flow are maximally equivalent. A potential ultrasonic transceiver would be KS-1640H12TR from Dongguan Cosson Electronic Plastic Co. A disadvantage of this particular device is the limited temperature range, up to 80° C. In some embodiments, waveguides and actively cooled transceivers are used to limit their temperature exposure.

FIG. 5A and FIG. 5B are block diagrams that illustrate two views of example acoustic actuator 560a and sensors 550a, 550b relative to a space between two stator vanes 540a and 540b, according to one embodiment. The acoustic source is an acoustic actuator (acoustic transmitter 560a) and the acoustic sensors are the acoustic receivers 550a, 550b. Both transmitter 560a and receivers 550a, 550b are configured within the stator space outer wall 518 so as not to intrude into the stator space between the two vanes 540a, 540b. To avoid a direct path from acoustic transmitter 560a to acoustic receivers 550b a, 550b, either the transmitter 560a or the receivers 550a, 550b, or both, are configured with a narrow acoustic beam 552. Then only the signals that have been reflected off the stator space inner wall 528 are received at the receivers 550a, 550b. Such reflected paths are depicted as paths 381a and 381b in FIG. 3B.

In the illustrated embodiment, the pair of sensors (receivers 550a and 550b) are symmetrically disposed equidistant from and on the same line with the acoustic actuator (transmitter 560a). This offers the advantage of simplified equations for separating gas temperature effects from gas velocity effects, as for example in simplified Equations 6c and 6d compared to more complex Equations 6a and 6b.

The distinctive signal is a prescribed set of acoustic frequencies of certain duration. In some embodiments, that duration is followed by a different prescribed set of frequencies for a second duration. In some embodiments, the prescribed frequencies of the second set are emitted by a different transmitter disposed at another stator stage.

Figure 6A:
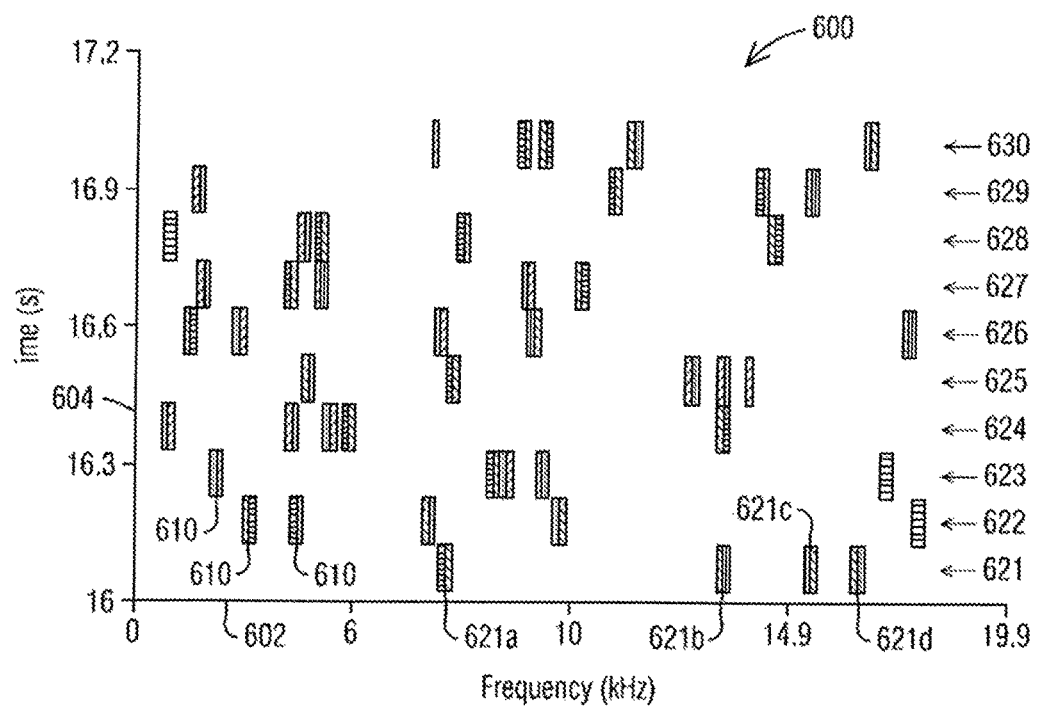
FIG. 6A is a graph that illustrates an example series of known acoustic signals that can be used alone or in combination by an acoustic actuator, according to various embodiments.

FIG. 6A is a graph that illustrates an example series of known acoustic signals that can be used alone or in combination by one or more acoustic actuators, according to various embodiments. As can be seen, the distinctive signals are depicted as distinct frequency marks, generally designated 610, that are spaced apart in frequency, i.e., are non-broadband, and are discontinuous in time. That is, a subgroup of distinct frequencies, e.g., four or five frequencies, are transmitted as a signal subgroup at a particular time for a short duration (about 100 milliseconds). Different signal subgroups are transmitted sequentially in time. The distinctive signal from one acoustic actuator (transmitter or transceiver) is made up of one or more subgroups. Different acoustic actuators use different sets of one or more subgroups. An alternative emitted waveform used in some embodiments is a linear chirp, which is a continuous change in frequency over a time interval.

As illustrated in FIG. 6A, each signal subgroup is designated as 621 through 630, and the frequency marks for signal subgroup 621, marking distinct frequencies, are designated as 621a, 621b, 621c, 621d. The corresponding received signal can be correlated with this signal to determine the time of maximum correlation. That time indicates the time that this signal reached that sensor and can be detected in the presence of noise and other sounds originating in the gas turbine engine.

Each successive signal subgroup 622 through 630 includes different distinct frequencies from the frequencies in the other signal subgroups. Hence, in addition to the signal subgroups 621-630 each forming a distinct identifiable pattern, or individual signature, along the frequency axis, the series of successive signal subgroups 621-630 also forms a distinct identifiable pattern, or overall signature, of frequencies along the time axis. Forming a signature of a plurality of the subgroups increases the distinctness of the signature, improves detectability, and provides a more precise autocorrelation peak in time, thus ensuring an accurate travel time measurement.

Figure 6B:
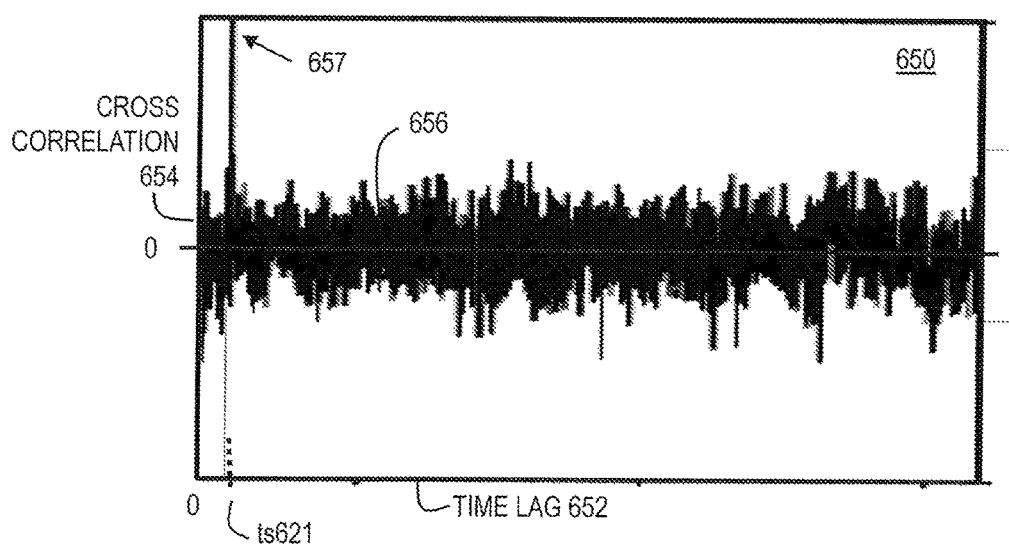
FIG. 6B is a graph that illustrates an example cross correlation between a known acoustic source signal and a detected signal at one sensor, according to an embodiment.

FIG. 6B is a graph 650 that illustrates an example cross correlation between a known acoustic source signal and a detected signal at one sensor, according to an embodiment. The horizontal axis 652 indicates time after transmittal of the acoustic source signal (e.g., signal 621), and the vertical axis 654 indicates cross correlation. The trace 656 give the cross correlation between the source signal and the detected signal at one sensor. The cross correlation is by definition a multiplication in the frequency domain. Note that there are many different correlation-based approaches available for time of flight estimation, including SCOT, PATH, ROTH etc. (See, for example, subdomain ee602 of domain wdfiles of category corn in folder local—files subfolder reportpresentations in file Group_19.) A significant peak 657 is detected in the trace 656 at the time lag ts621 that corresponds to the travel time of signal 621 along the reflected acoustic path (e.g., 381a) from source to sensor. This value ts621 is used as one of the travel times in the computation of gas temperature and gas velocity, e.g., is used as ts1 in one or more of Equation 6a, Equation 6b, Equation 6c, Equation 6d or Equation 7.

Although the illustrated embodiment in FIG. 5A and FIG. 5B includes the minimal configuration of one acoustic transmitter 560a and two acoustic receivers 550a and 550b, depending on the spatial resolution desired and the accessibility of the component, in other embodiments the number of transmitters and receivers are increased to achieve a target spatial resolution. The signal emitted from the transmitters is designed to be distinguishable when being detected over the existing acoustic noise found in the cascade (blade flutter and flow noise, etc.) and the signal from different actuators (e.g., using different subgroups); this distinctive signal is repeated to provide temporal resolution.

The received signal is processed using advanced spectral and other signal processing techniques in control system 170 and is used by temperature/velocity detection module 180 to derive the measured temperature and velocity in real time, e.g., using Equations 6c and 6d, above. This sensor arrangement is repeated for every stage where the measurement is desired, and the same multi-channel electronic signal acquisition and processing system (e.g., control system 170) can accommodate sensor systems from several stages.

FIG. 7 is a flow chart that illustrates an example method for using a known signal in a space between two stator vanes, according to an embodiment. In step 701, analogous to step 401 described above, an acoustic actuator (e.g., acoustic transmitter 560a) is mounted as an acoustic source nonintrusively in a wall of the space between two stator vanes so as to emit an acoustic signal into the space. In some embodiments, the step is repeated for multiple pairs of stator vanes on one or more different stators in the compressor or turbine sections or both. In step 703, analogous to step 403 described above, a pair of acoustic sensors (e.g., acoustic receivers 550a, 550b) is mounted nonintrusively in a wall of the space so as to detect an acoustic signal received from the space, for the same pairs of stator vanes where the acoustic sources are mounted. At least one sensor in each pair is displaced with a distance component downstream of the other relative to the gas flow in the space. That is, a first acoustic sensor is displaced a first distance from a different second acoustic sensor of the plurality of acoustic sensors in a first direction parallel to a direction of fluid flow through the space.

In step 705, analogous to step 405 described above, each acoustic source (e.g., acoustic transmitter 560a) is operated by the control system 170 to emit a distinctive acoustic signal (e.g., subgroup 621 for transmitter 560a) that can be distinguished from other acoustic signals (e.g., from other acoustic transmitters emitting other signals made up of one or more other subgroups) and ambient sounds in the gas flow space between the two stator vanes for the same pairs of stator vanes. In step 707, analogous to step 407, a received acoustic signal is detected at the pair of acoustic sensors for each pair of stator vanes and recorded by the control system 170.

In step 709, analogous to step 409, a difference in travel time (time of flight) is determined by the module 180 for the next pair of paths between each source and each pair of receivers, at least in the space between the same adjacent pair of stator vanes. For example, the cross correlation is computed between the source signal and the detected signals at each of the pair of sensors, to get a travel time to each sensor. The two travel times are then differenced to get the travel time difference.

In step 711, analogous to step 411, a gas flow temperature in the space between the pair of adjacent stator vanes for the current pair of paths is determined by the module 180 based on a sum of the two travel times for the current pair of sensors. For example, the two travel times are used with Equation 6b or Equation 6d to determine the sound speed and the sound speed is used to compute d/t in Equation 1a to determine the temperature.

In step 713, analogous to step 413, a gas flow velocity in the space between each pair of adjacent stator vanes is determined by the module 180 based on a difference of the two travel times for the current pair of sensors. For example, the two travel times are used with Equation 6a or Equation 6c.

In step 715 it is determined by module 180 whether there is another pair of acoustic paths, and in step 717 it is determined by module 180 whether there is another pair of adjacent stator vanes to process, analogous to steps 415 and 417. In some embodiments, the temperatures and velocities derived over multiple paths through the same space are used with tomography methods by module 180 to deduce a distribution of temperatures and velocities, as describe above in step 421.

In some embodiments, there is a need for measuring bulk temperature and velocity as well as axial distribution of temperature and velocity for component and blade design validation as well as for engine performance assessment. This is true for both existing engine frames as well as new frames that are being designed for higher efficiency and lower emissions.

Figure 8A:
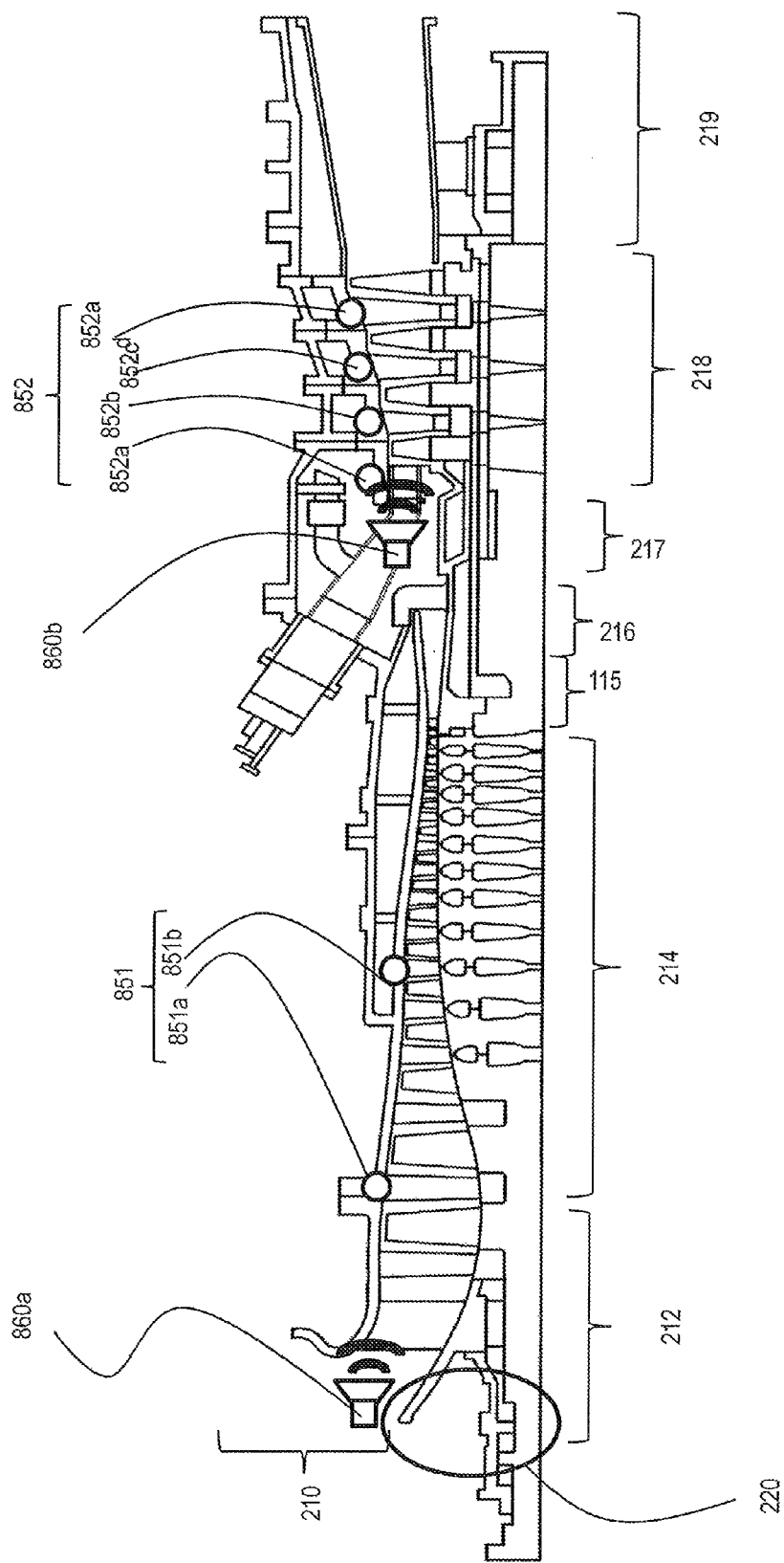
FIG. 8A and FIG. 8B are block diagrams that illustrate two example configurations of acoustic actuators and sensors relative to several spaces for gas flow among multiple stators and rotors, according to various embodiments.
Figure 8B:
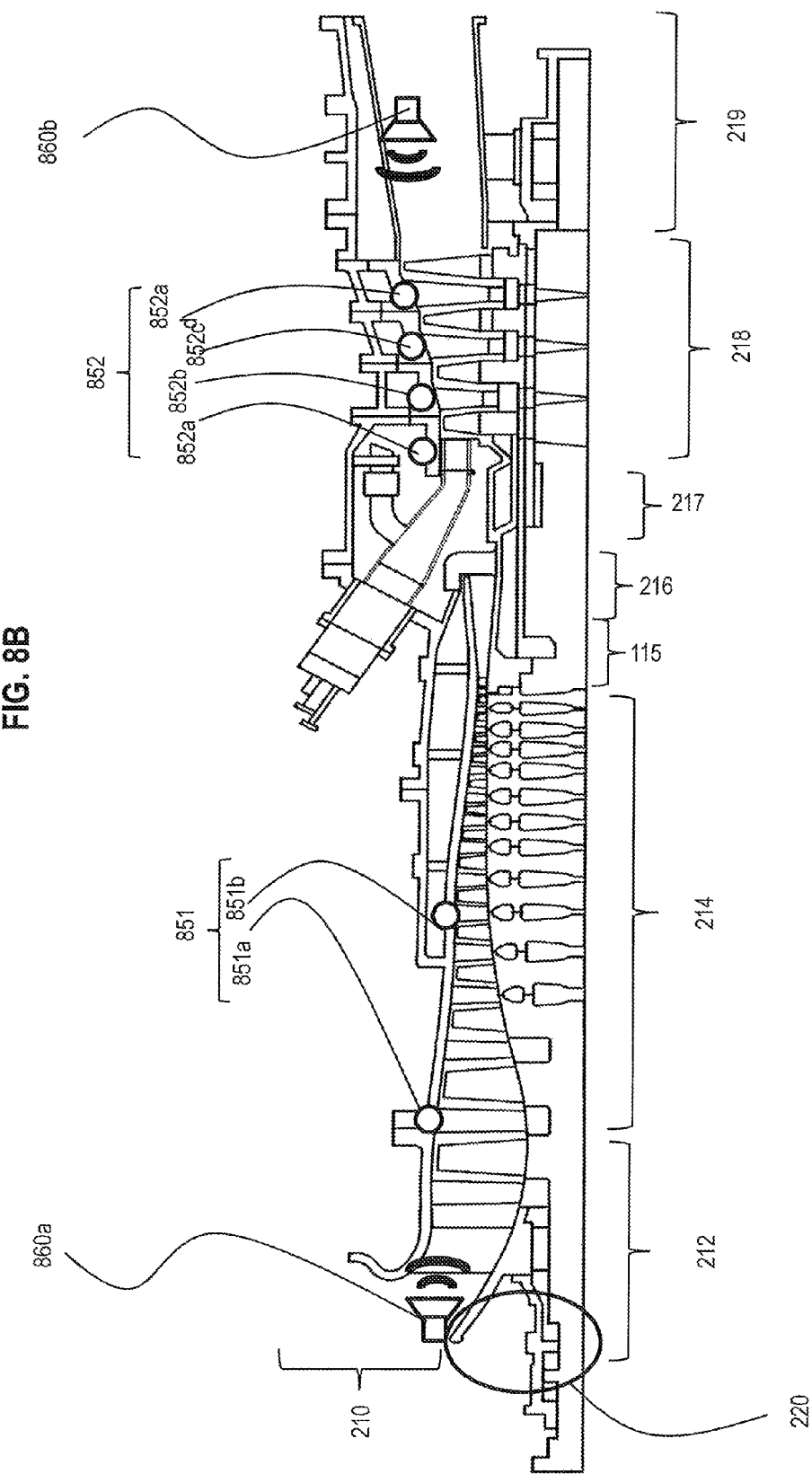

These next embodiments utilize an acoustic seeding method which involves continuously sending acoustic signals that are specifically designed for easy detection along the gas flow upstream and downstream directions with the aid of acoustic transmitters that are located upstream and downstream of the component (turbine section or compressor section). FIG. 8A and FIG. 8B are block diagrams that illustrate two example configurations of acoustic actuators and sensors relative to several spaces for gas flow among multiple stators and rotors, according to various embodiments.

In one of these next embodiments, depicted in FIG. 8A, acoustic transmitters are installed at the intake of the engine, upstream (at least in the axial component) of the inlet guide vanes and upstream (in the axial component) of the rotors of the turbine section. FIG. 8A shows the same upper cross section as depicted in FIG. 2A. The housing 210, shaft assembly 220, inlet section 212, compressor section 214, compressor diffuser section 214, combustion section 216, transition section 217, turbine section 218 and exhaust section 219 are as described above with reference to FIG. 2A. In this embodiment two acoustic actuators are installed, one acoustic actuator 860a in the inlet section 212 and one acoustic actuator 860b in the transition section 217, so as not to intrude into the spaces of gas flow that are to be monitored for temperature and velocity. Both actuators are configured to emit distinctive acoustic signals, at least in a downstream (axial component) direction. Thus travel time is measured primarily in an axial direction.

Acoustic sensors 851a and 851b (collectively referenced hereinafter as compressor section sensors 851) and acoustic sensors 852a, 852b, 852c, 852d (collectively referenced hereinafter as turbine section sensors 852) are collectively referenced hereinafter as acoustic sensors 850. The acoustic sensors 850 are installed nonintrusively at stators where one is interested in measuring the temperature and velocity, e.g., between at least one pair of adjacent stator vanes on the stator. In the illustrated embodiment, two compressor section acoustic sensors 851 are disposed at stators that are four stages apart in the compressor section 214, and four turbine section acoustic sensors 852 are disposed on every stator stage of the turbine section 218. If the interest is characterizing all the stages of compressor and turbine, then the receivers would be installed at each stator. If only temperature is of interest, the acoustic actuator 860a on the inlet section 112 is sufficient. Recall that one can measure the temperature alone without the velocity component by using one source and one receiver spaced apart orthogonal to the flow direction. This way the flow doesn't affect the time of flight. Also, note that the effect of velocity is much lower than the temperature effect, satisfying the inequality in expression 4f. Therefore, if the source and receiver are close together (e.g., if a single transceiver is used) then one can disregard the velocity effect. A second acoustic actuator 860b is included to have sufficient signal strength in the turbine section 218.

In a case where both temperature and velocity at each stator stage of interest are desired, then two directions of travel in the same space are desired, and acoustic seeding in both directions is used. FIG. 8B is like FIG. 8A, except that the second acoustic actuator 860b is installed in the exhaust section 219 and is directed to send acoustic signals upstream against the axial component of the gas flow.

The received acoustic signal at each stage is processed, first to detect that signal above all different acoustic sounds and noise floor that are prevalent in any operating engine (e.g., rotor blade rotation frequencies), and then to process it to relate the changed acoustic characteristics to the target parameters, in this case velocity and temperature. The acoustic seeding is done at high speeds continuously and therefore these measurements are available real time at update rates of around one measurement per second.

For example, in FIG. 8A, to monitor the space between two acoustic sensors (e.g., sensors 851 and 851b) the travel time between the two sensors is determined. For example, an earlier time is determined based on a time when the distinctive signal from actuator 860a causes a correlation peak at the closer sensor (e.g., sensor 851a); and, a later time is determined based on a time when the distinctive signal from actuator 860a causes a correlation peak at the farther sensor (e.g., sensor 851b). Subtracting the earlier time from the later time gives the travel time of the signal from the closer sensor to the farther sensor. This is based on the average temperature and average gas velocity along the path in the space between the two sensors. The paths can be assumed to be known or equal to the axial distance from source to receiver or based on modeling using ray tracing techniques. If the average gas velocity in the space is known or assumed or measured separately, then the sound speed can be determined by dividing the travel time between the sensors by the path length difference between the sensors corrected for the assumed velocity along the path between the two sensors. The average temperature T in the space can be determined from the computed sound speed using Equation 1a and substituting sound speed for the ratio d/t.

In an embodiment, both temperature and velocity are determined from the same acoustic measurements. In these embodiments, a second travel time is measured between the same two sensors based on a different source, e.g., acoustic actuator 860b, as depicted in either FIG. 8A or, preferably, as depicted in FIG. 8B. Thus in this embodiment at least two acoustic actuators are used. Unlike the embodiments described above where the source is located in the same space as the sensors and a single source can be used with two sensors, when the sources are so far away, much of the path between source and receiver is outside the space of interest and in different stages where the velocity and temperatures are quite different. Thus the assumption of constant temperature and velocity is very poor. Therefore, the two paths from the same source are not used to characterize the temperature and velocity in the vicinity of the sensors. Instead, another path through the same space is used. That path is the path between the same two sensors from the different source, actuator 860b. The travel time between the two sensors from the first source (e.g., 860a) is used as ts1; and, the travel time between the two sensors from the second source (e.g., 860b) is used as ts2.

Then both the temperature and gas velocity in the space between the two sensors can be determined using the two measured travel times, e.g., using Equation 6a and Equation 6b, or Equation 6c and Equation 6d. Because of the large axial separations, the axial components of the paths dominate; so, in some embodiments, the example Equations are further simplified by assuming $\beta=\beta1\approx\beta2\approx0$, thus $\cos(\beta)\approx1$, and $\alpha1\approx\theta$, and $\alpha2\approx\theta+180$.

These embodiments allow the temperature and velocity to be measured in paths passing through rotating rotor blades. Several of these embodiments take advantage of innovative placement of the acoustic transmitters and receivers, along with distinctive actuator signals to isolate the measurement from unwanted signals, to relate detected signals to the desired values of temperature and/or velocity at any position within the gas flow portion of the engine. These kinds of embodiments provide the capability for cost effectively and accurately measuring thermal efficiency and performance of each stage of turbine (and/or compressor) to quickly and efficiently validate design changes to blades and vanes as well as new engine frames.

Figure 9A:
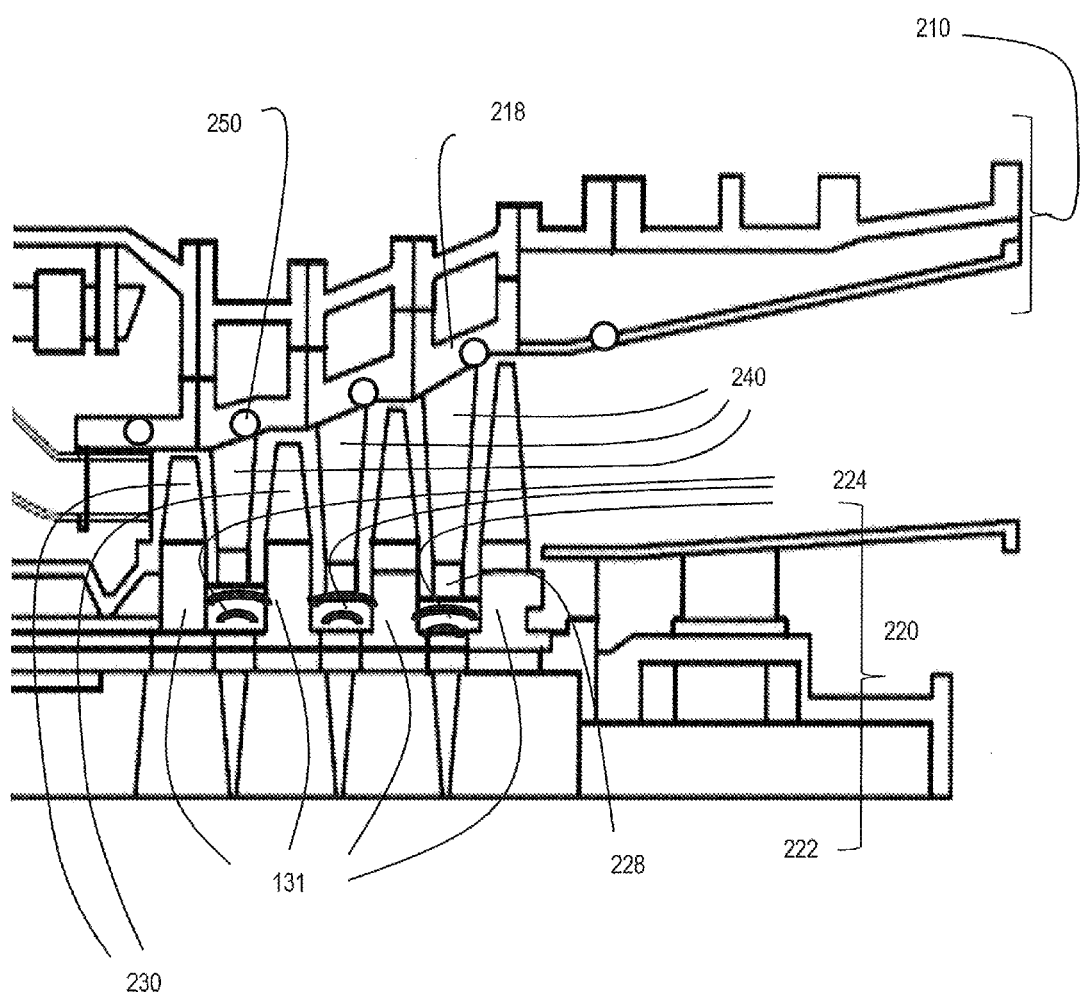
FIG. 9A and FIG. 9B are block diagrams that illustrate two example configurations of sensors with passive acoustic sources relative to several spaces for gas flow among multiple stators in a turbine section, according to various embodiments.
Figure 9B:
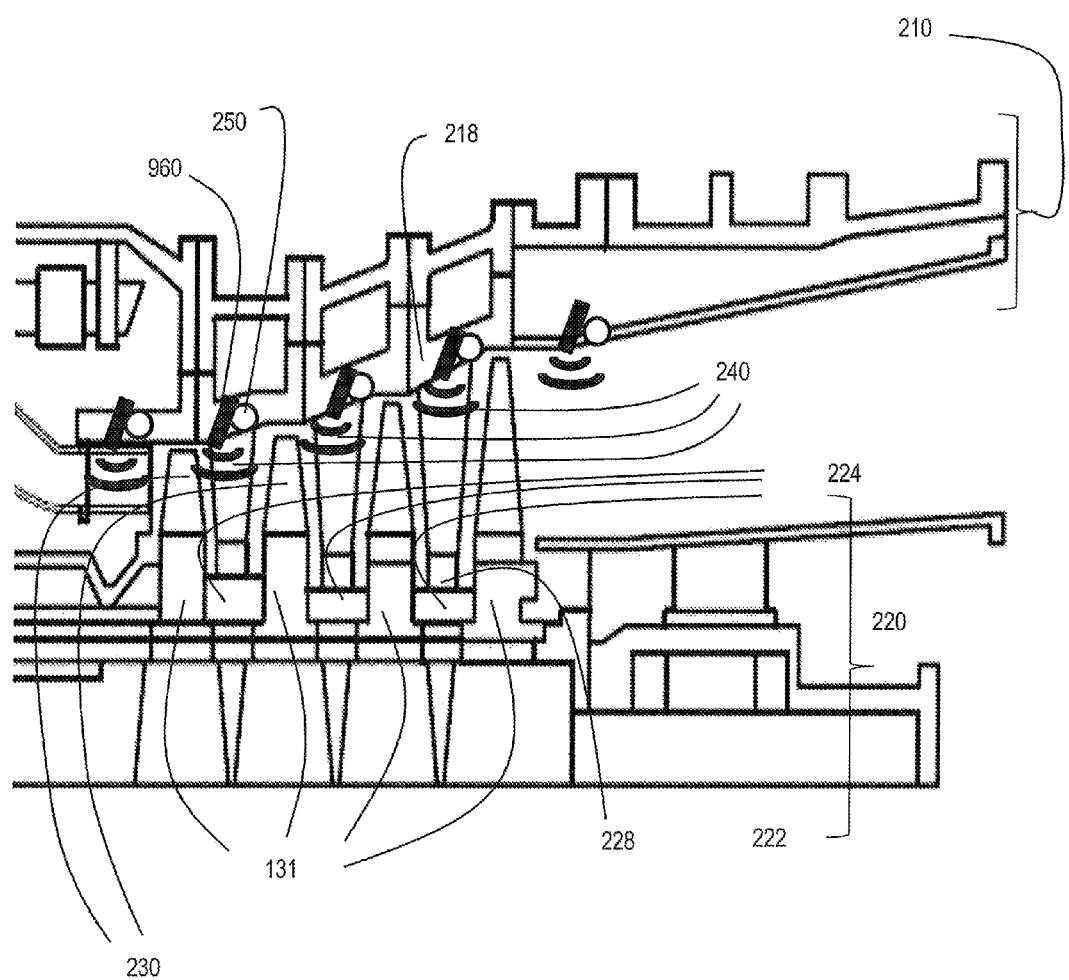

The more acoustic transducers disposed in the gas turbine engine, in the form of acoustic actuators and sensors, the greater are the demands for maintenance and the greater are the opportunities for failure, especially in the high temperature environment of the turbine section. Thus it is advantageous in some embodiments to eliminate one or more sensors or actuators and still obtain a sufficient number of acoustic paths through the gas flow spaces of interest. In these embodiments, passive acoustic sources, such as indigenous signals or low-maintenance resonator sticks, are used in place of one or more acoustic actuators employed in the embodiments described above. FIG. 9A and FIG. 9B are block diagrams that illustrate two example configurations of sensors with passive acoustic sources relative to several spaces for gas flow among multiple stators in a turbine section, according to various embodiments.

In the embodiments described with reference to FIG. 9A, the acoustic vibrations and resonances of internal cavities of the turbine are used as acoustic sources to measure the velocity and temperature. Acoustic waves created by these internal cavities' dominant vibrations are tracked across the gas flow and measured on the outer surface of the gas flow. The properties of the detected acoustic signal are used to determine the temperature of the gas flow and hence the speed of sound in the gas flow, while that sound speed and the differences in the time it takes for the acoustic waves to cross the hot gas flow to two different sensors are used to determine the velocity of the gas flow. This can be achieved at each stage of the turbine section (as well as each stage of the compressor section) by just placing highly sensitive, high temperature resistant sensors (microphones) that are connected to the control system 170 with high speed data acquisition units.

For example, a pair of sensors is deployed between adjacent stator vanes of a stator stage for each of one or more pairs on the same or different stator stages. In module 180 real time or near real time data processing is performed to provide the temperature and pressure values. Bulk mean temperature and velocity can be achieved with a single pair of sensors for each space, but for spatially resolving these and to obtain profiles or maps within the space, several pairs of receivers (microphones) are used for each space.

FIG. 9A depicts a portion of a gas turbine engine as outlined in a dotted line in FIG. 2A. The housing 210 with stator space outer wall 218, and the sensors 250, and the shaft assembly 220 with axial shaft 222, rotors 131, cavities 224 and stator space inner walls 228, and the stator vanes 240 and rotor blades 230 are as described above with reference to FIG. 2B. Missing from FIG. 9A are the acoustic actuators 260. Instead, sounds emanating from the cavities 224 are used as acoustic sources.

Because the sounds emanating from cavities 224 are continuous, there is no acoustic event corresponding to a subgroup of FIG. 6A, such as subgroup 621, whose arrival can be detected at the sensors 250. Thus individual travel times corresponding to ts1 and ts2 cannot be measured. However the sound emanating from each of the cavities 224 includes a peak at a resonant frequency of the cavity. This peak is easily determined in the detected signal at the nearby sensors 250. This resonant peak is at a frequency given by the dimension of the cavity Dc divided into the speed of sound in the cavity, Sc, which is related to the temperature Tc in the cavity as given by Equation 1a. That is, the resonant frequency $F_R$ is given by Equation 8a:

$$F_R=Sc/Dc \quad (8a)$$

where Dc is known. If f is the function of Equation 1a, replacing ratio d/t by the sound speed Sc, then the temperature of the cavity is given by Equation 8b:

$$Tc=f(Sc)=f(Dc*F_R) \quad (8b)$$

In a gas turbine engine, the sound speed variations from initial temperatures to operating temperatures can increase from about 340 meters per second (m/s) at ambient temperatures to about 600 m/s. at operating temperatures. The dimensions Dc of the cavities 224 vary in different parts of the engine from about 0.1 meters to about 1 meter. Because adjacent cavities are of different sizes, there is expected to be a different resonant frequency for each cavity even at the same temperature; so, the acoustic signals from the different cavities 224 are distinct.

The temperature in the cavity Tc is, at least to first order, related to the temperature in the gas flow above the cavity, which provides the heat that warms the cavity. For example, if the temperature of the gas flow in the space between stator vanes is Ts, then Tc=C*Ts, where C is a coefficient with a value between zero and 1. In various embodiments, the value of C is known by previous experiment or by simulation. Thus the resonant frequency is related to the temperature of the gas in the space above the cavity. Equation 8c is a very simplified equation that illustrates the relationship between the temperature of the gas flow in the space and the resonant frequency.

$$Ts=Tc/C=f(Sc)/C=f(Dc*F_R)/C \quad (8c)$$

In many embodiments, the different cavities have different shapes and dimensions Dc, and each cavity may have several dimensions, such as the dimension of the axial diameter of the cavity and the dimension of the radial diameter of the cavity. All can lead to different frequency peaks $F_R$ in the detected signal. The formula for the resonance frequency is dependent on the physical shape of the resonator (e.g., open cylinder, cone, rectangular). The speed of sound is dependent on the temperature and thus the frequency changes based on the temperature. However, the temperature change is dependent on the shape and dimensions of the resonator.

Once Ts is determined, the sound speed in the gas flow, Ss, can be determined by inverting Equation 1a, as given by Equation 9.

$$Ss=B\sqrt{\{Ts+273.16\}} \quad (9)$$

This gas flow sound speed Ss can be used with Equation 7 to determine the velocity, V, of the gas flow provided the travel time difference (ts2−ts1) can be determined. As shown below, the travel time difference can be determined from the phase spectrum of the detected signals at the two sensors even without determining the individual travel times.

FIG. 10A and FIG. 10B are graphs that illustrate example spectral amplitudes of a signal from one sensor and spectral phases of two signals from different sensors for determining temperature and velocity of gas flow in a space, according to one embodiment. FIG. 10A is a graph 1010 of an example spectrum of acoustic fluctuations detected at one of the two sensors in the space. The horizontal axis 1012 indicates frequency in relative units; and, the vertical axis 1014 indicates the amplitude in arbitrary units. Trace 1016 is the amplitude spectrum. Several peaks are evident in the spectrum 1016. For purposes of illustration, it is assumed that peaks 1017a, 1017b and 1017c indicate the resonant peaks from three nearby cavities, with the peak 1017a from the nearest cavity.

Based on this frequency of peak 1017a and the known dimension Dc of the nearest cavity, the temperature Tc of the cavity is deduced (Equation 8b). Based on this and the known constant C, the temperature Ts of the gas flow is determined (Equation 8c). Based on this gas flow temperature, Ts, the speed of sound in the gas Ss is determined (Equation 9).

FIG. 10B is a graph 1020 that illustrates an example phase spectrum determined by combining the detected signals at two different sensors. The horizontal axis 1012 is the same as in FIG. 10A; and, the vertical axis indicates phase φ in relative units. The phase φ at any frequency indicates the difference in the timing of the peaks of that frequency at the two sensors and falls in a range from −180 to +180 in degrees (or, −π to π in radians). For purposes of illustration, it is assumed that the trace 1026 indicates the phase spectrum of the two sensors closest to the cavity that causes peak 1017a in FIG. 10A. A non-zero phase is due to a travel time difference modulated by the period $P_R=(1/F_R)$ associated with the frequency, as given by Equation 10a for phase in degrees.

$$\varphi/\{360*F_R\}=\text{mod}\{(ts2-ts1), 1/F_R\} \quad (10a)$$

Which implies the relationship given by Equation 10b:

$$(ts2-ts1)=(N+\varphi/360)/F_R \text{ for } N=0, 1, \quad (10b)$$

Plugging these travel time differences into Equation 7 and solving using the quadratic formula, various values for the velocity V of the gas flow are obtained. One or more of the choices for the value of N can be eliminated as unreasonable by various criteria, e.g., by not falling in an expected range of permitted velocities.

For example, for a resonant frequency $F_R$=100 Hz, the period $P_R$=0.01 seconds. A phase of 90 degrees implies the two peaks are off by one quarter (90/360) of the period, or 0.0025 seconds. The time difference is then either 0.0025 seconds or 0.0125 seconds or 0.0225 seconds, etc., as given by Equation 10b.

$$(ts2-ts1) = (N+0.25)*0.01 = 0.25*0.01 + N*0.01 \text{ for } N = 0,$$
$$1, 2, \ldots = 0.0025, 0.0125, 0.0225, \ldots$$

Thus in this embodiment, step 401 is omitted. In step 403 the acoustic sensors 250 are mounted nonintrusively as depicted in FIG. 10A. In step 405 the gas turbine engine is fired up to cause the cavities 224 to resonate. In step 407 the resonant peaks (e.g., 1017a, 1017b, 1017c) are determined in the detected signal. In step 409, the travel time difference is determined based on the phase φ associated with the resonant frequency $F_R$, e.g., according to Equation 10b. In step 411 the temperature Ts of the gas flow is determined based on at least one of the detected signals, e.g., using $F_R$ and Equation 8c. In step 413, the gas flow velocity is determined by determining the gas flow sound speed based on the gas flow temperature Ts using Equation 9; then, the gas flow sound speed Ss and the travel time difference from the phase φ are used with Equation 7 to determine V.

In another embodiment, instead of relying on the hidden cavities 224, resonator sticks are installed near the acoustic sensors 250 next to the space to be monitored, without intruding into the space. A resonator stick is a passive resonating device that could be excited by a remotely placed acoustic transmitter at high frequencies. Even ultrasonic frequencies could be utilized for this application.

FIG. 9B depicts the same portion of a gas turbine engine as in FIG. 9A. The housing 210 with stator space outer wall 218, and the sensors 250, and the shaft assembly 220 with axial shaft 222, rotors 131, cavities 224 and stator space inner walls 228, and the stator vanes 240 and rotor blades 230 are as described above with reference to FIG. 2B. Still missing from FIG. 9A are the acoustic actuators 260. Instead, passive resonator sticks 960 are used as acoustic sources. Each resonator stick 960 is configured to resonate at a different acoustic frequency at an amplitude far above the amplitude of those same frequencies during normal operation of the gas turbine engine. Thus each resonator stick emits a distinctive acoustic source signal into the space.

Because the sounds emanating from resonator sticks 224 can be actively initiated, there is an acoustic event corresponding to a subgroup of FIG. 6A, whose arrival can be detected at the sensors 250. Thus individual travel times corresponding to ts1 and ts2 can be measured. The process is similar to the one described above with respect to FIG. 7. However, this method offers the advantages of having a relatively simple device inserted in the upper wall of the space to be monitored instead of a precision acoustic actuator. The advantages that accrue include reducing any or all of the cost of the device, the maintenance effort, the maintenance cost, and the opportunities for failure. In some embodiments, the acoustic receiver close to the resonator stick can both record the emitted signal as well as the reflection and monitor the time delay peak in the autocorrelation function for temperature measurement.

In some embodiments, relative changes in fluid flow velocity are sufficient for determining the operation of the gas turbine engine. In some embodiments of this kind, both temperature and relative change in velocity can be monitored with a single transceiver. For example, in some embodiments, a transceiver replacing one or more of the sensors 250 depicted in FIG. 9A can be used to monitor both fluid flow velocity changes and fluid flow temperature in the adjacent space of gas flow. In some of these embodiments, the processor is configured to cause the acoustic transceiver mounted in a first wall of a space of fluid flow in the gas turbine engine, without extending into the space, to emit a first acoustic signal into the space and detect received acoustic signals from the space. The processor then determines a travel time of the first acoustic signal received at the transceiver after reflection from a different second wall of the space. Then the processor determines a temperature of fluid flow in the space based on the travel time. This is because the outbound and inbound portions of the acoustic path have fluid velocity effects cancel out and the travel time is based essentially on the sound speed along the path and hence the temperature of the fluid in the fluid flow. The processor also determines in the received acoustic signals a temporal change of phase of a resonant acoustic frequency of a cavity in a shaft assembly in a turbine section of the gas turbine engine (e.g., of a cavity 224 in FIG. 9A that is displaced in the direction of fluid flow from the transceiver). The processor determines a temporal change in velocity of fluid flow in the space based on the temporal change of phase of the resonant acoustic frequency. This is because, after correcting for temperature changes determined by the reflected first signal, each residual phase change is due to the change in fluid flow velocity along the path.

FIG. 11 is a block diagram that illustrates a computer system 1100 upon which an embodiment of the invention may be implemented. Computer system 1100 includes a communication mechanism such as a bus 1110 for passing information between other internal and external components of the computer system 1100. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1100, or a portion thereof, constitutes a means for performing one or more steps of one or more methods described herein.

A sequence of binary digits constitutes digital data that is used to represent a number or code for a character. A bus 1110 includes many parallel conductors of information so that information is transferred quickly among devices coupled to the bus 1110. One or more processors 1102 for processing information are coupled with the bus 1110. A processor 1102 performs a set of operations on information. The set of operations include bringing information in from the bus 1110 and placing information on the bus 1110. The set of operations also typically include comparing two or more units of information, shifting positions of units of information, and combining two or more units of information, such as by addition or multiplication. A sequence of operations to be executed by the processor 1102 constitutes computer instructions.

Computer system 1100 also includes a memory 1104 coupled to bus 1110. The memory 1104, such as a random access memory (RAM) or other dynamic storage device, stores information including computer instructions. Dynamic memory allows information stored therein to be changed by the computer system 1100. RAM allows a unit of information stored at a location called a memory address to be stored and retrieved independently of information at neighboring addresses. The memory 1104 is also used by the processor 1102 to store temporary values during execution of computer instructions. The computer system 1100 also includes a read only memory (ROM) 1106 or other static storage device coupled to the bus 1110 for storing static information, including instructions, that is not changed by the computer system 1100. Also coupled to bus 1110 is a non-volatile (persistent) storage device 1108, such as a magnetic disk or optical disk, for storing information, including instructions, that persists even when the computer system 1100 is turned off or otherwise loses power.

Information, including instructions, is provided to the bus 1110 for use by the processor from an external input device 1112, such as a keyboard containing alphanumeric keys operated by a human user, or a sensor. A sensor detects conditions in its vicinity and transforms those detections into signals compatible with the signals used to represent information in computer system 1100. Other external devices coupled to bus 1110, used primarily for interacting with humans, include a display device 1114, such as a cathode ray tube (CRT) or a liquid crystal display (LCD), for presenting images, and a pointing device 1116, such as a mouse or a trackball or cursor direction keys, for controlling a position of a small cursor image presented on the display 1114 and issuing commands associated with graphical elements presented on the display 1114.

In the illustrated embodiment, special purpose hardware, such as an application specific integrated circuit (IC) 1120, is coupled to bus 1110. The special purpose hardware is configured to perform operations not performed by processor 1102 quickly enough for special purposes. Examples of application specific ICs include graphics accelerator cards for generating images for display 1114, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1100 also includes one or more instances of a communications interface 1170 coupled to bus 1110. Communication interface 1170 provides a two-way communication coupling to a variety of external devices that operate with their own processors, such as printers, scanners and external disks. In general the coupling is with a network link 1178 that is connected to a local network 1180 to which a variety of external devices with their own processors are connected. For example, communication interface 1170 may be a parallel port or a serial port or a universal serial bus (USB) port on a personal computer. In some embodiments, communications interface 1170 is an integrated services digital network (ISDN) card or a digital subscriber line (DSL) card or a telephone modem that provides an information communication connection to a corresponding type of telephone line. In some embodiments, a communication interface 1170 is a cable modem that converts signals on bus 1110 into signals for a communication connection over a coaxial cable or into optical signals for a communication connection over a fiber optic cable. As another example, communications interface 1170 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1170 sends and receives electrical, acoustic or electromagnetic signals, including infrared and optical signals, which carry information streams, such as digital data.

The term computer-readable medium is used herein to refer to any medium that participates in providing information to processor 1102, including instructions for execution. Such a medium may take many forms, including, but not limited to, non-volatile media, volatile media and transmission media. Non-volatile media include, for example, optical or magnetic disks, such as storage device 1108. Volatile media include, for example, dynamic memory 1104. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1102, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1102, except for carrier waves and other signals.

Logic encoded in one or more tangible media includes one or both of processor instructions on a computer-readable storage media and special purpose hardware, such as ASIC 1120.

Network link 1178 typically provides information communication through one or more networks to other devices that use or process the information. For example, network link 1178 may provide a connection through local network 1180 to a host computer 1182 or to equipment 1184 operated by an Internet Service Provider (ISP). ISP equipment 1184 in turn provides data communication services through the public, world-wide packet-switching communication network of networks now commonly referred to as the Internet 1190. A computer called a server 1192 connected to the Internet provides a service in response to information received over the Internet. For example, server 1192 provides information representing video data for presentation at display 1114.

The invention is related to the use of computer system 1100 for implementing the techniques described herein. According to one embodiment of the invention, those techniques are performed by computer system 1100 in response to processor 1102 executing one or more sequences of one or more instructions contained in memory 1104. Such instructions, also called software and program code, may be read into memory 1104 from another computer-readable medium such as storage device 1108. Execution of the sequences of instructions contained in memory 1104 causes processor 1102 to perform the method steps described herein. In alternative embodiments, hardware, such as application specific integrated circuit 1120, may be used in place of or in combination with software to implement the invention. Thus, embodiments of the invention are not limited to any specific combination of hardware and software.

The signals transmitted over network link 1178 and other networks through communications interface 1170, carry information to and from computer system 1100. Computer system 1100 can send and receive information, including program code, through the networks 1180, 1190 among others, through network link 1178 and communications interface 1170. In an example using the Internet 1190, a server 1192 transmits program code for a particular application, requested by a message sent from computer 1100, through Internet 1190, ISP equipment 1184, local network 1180 and communications interface 1170. The received code may be executed by processor 1102 as it is received, or may be stored in storage device 1108 or other non-volatile storage for later execution, or both. In this manner, computer system 1100 may obtain application program code in the form of a signal on a carrier wave.

Various forms of computer readable media may be involved in carrying one or more sequence of instructions or data or both to processor 1102 for execution. For example, instructions and data may initially be carried on a magnetic disk of a remote computer such as host 1182. The remote computer loads the instructions and data into its dynamic memory and sends the instructions and data over a telephone line using a modem. A modem local to the computer system 1100 receives the instructions and data on a telephone line and uses an infra-red transmitter to convert the instructions and data to a signal on an infra-red a carrier wave serving as the network link 1178. An infrared detector serving as communications interface 1170 receives the instructions and data carried in the infrared signal and places information representing the instructions and data onto bus 1110. Bus 1110 carries the information to memory 1104 from which processor 1102 retrieves and executes the instructions using some of the data sent with the instructions. The instructions and data received in memory 1104 may optionally be stored on storage device 1108, either before or after execution by the processor 1102.

FIG. 12 illustrates a chip set 1200 upon which an embodiment of the invention may be implemented. Chip set 1200 is programmed to perform one or more steps of a method described herein and includes, for instance, the processor and memory components described with respect to FIG. 11 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1200, or a portion thereof, constitutes a means for performing one or more steps of a method described herein.

In one embodiment, the chip set 1200 includes a communication mechanism such as a bus 1201 for passing information among the components of the chip set 1200. A processor 1203 has connectivity to the bus 1201 to execute instructions and process information stored in, for example, a memory 1205. The processor 1203 may include one or more processing cores with each core configured to perform independently. A multi-core processor enables multiprocessing within a single physical package. Examples of a multi-core processor include two, four, eight, or greater numbers of processing cores. Alternatively or in addition, the processor 1203 may include one or more microprocessors configured in tandem via the bus 1201 to enable independent execution of instructions, pipelining, and multithreading. The processor 1203 may also be accompanied with one or more specialized components to perform certain processing functions and tasks such as one or more digital signal processors (DSP) 1207, or one or more application-specific integrated circuits (ASIC) 1209. A DSP 1207 typically is configured to process real-world signals (e.g., sound) in real time independently of the processor 1203. Similarly, an ASIC 1209 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1203 and accompanying components have connectivity to the memory 1205 via the bus 1201. The memory 1205 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1205 also stores the data associated with or generated by the execution of one or more steps of the methods described herein.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The invention claimed is:

1. A system comprising:
a gas turbine engine comprising a plurality of stators and rotors, each stator comprising a plurality of stator vanes and each rotor comprising a plurality of rotor blades, each rotor configured to rotate about a shaft assembly that comprises an axial shaft rigidly connected to each rotor and configured to rotate around a long axis of the axial shaft;
a plurality of acoustic sensors mounted to detect acoustic signals in a space of gas flow in the gas turbine engine without extending into the space, wherein a first acoustic sensor of the plurality of acoustic sensors is displaced a first distance from a different second acoustic sensor of the plurality of acoustic sensors in a first direction parallel to a direction of fluid flow through the space; and
a processor in electrical communication with the plurality of acoustic sensors, the processor configured to perform at least the steps of:
detecting a first acoustic signal at the first acoustic sensor and a second acoustic signal at the second acoustic sensor;
determining a first travel time difference between the first acoustic sensor and the second acoustic sensor based on the first acoustic signal and the second acoustic signal;
determining a velocity of fluid flow in the space based at least in part on the first travel time difference; and
determining a temperature of fluid flow in the space based at least in part on either the first acoustic signal or the second acoustic signal or both,
an acoustic source mounted to introduce a known acoustic signal into the space without extending into the space, wherein:
determining the first travel time difference further comprises determining a difference between a first travel time and a second travel time, further comprising determining the first travel time based on a time the known acoustic signal is introduced into the space and a time of peak correlation of the known signal at the first sensor, and determining the second travel time based on the time the known signal is introduced into the space and a time of peak correlation of the known signal at the second acoustic sensor; and
determining the temperature in the space further comprises determining the temperature based on a sum of the first travel time and the second travel time and a sum of a first length of a first path from the acoustic source to the first acoustic sensor and a second length of a second path from the acoustic source to the second acoustic sensor,
wherein based on the determined temperature and velocity of fluid flow, profiles of temperature and velocity, respectively, are generated and utilized by the processor to ensure the gas turbine engine is operating within specified ranges, and
wherein when the gas turbine is not operating within the specified ranges, adjustments are made within the gas turbine to attain improved performance of the engine.

2. A system as recited in claim 1, wherein a resonant acoustic frequency of a cavity in the shaft assembly in a turbine section of the gas turbine engine is associated with a temperature of fluid flow in the space, and determining the temperature of the fluid flow in the space further comprises determining a frequency of a resonant peak in a spectrum of the first acoustic signal or a spectrum of the second acoustic signal or both.

3. A system as recited in claim 2, wherein determining the first travel time difference further comprises determining a phase value of a phase spectrum of the first acoustic signal and the second acoustic signal at the frequency of the resonant peak, and dividing the phase value by the frequency of the resonant peak.

4. A system as recited in claim 1, wherein the acoustic source is a resonator stick that is caused to emit the known acoustic signal in response to an acoustic activation signal at the time the known signal is introduced.

5. A system as recited in claim 1, wherein the known acoustic signal is distinct from all acoustic signals expected to be generated by the gas turbine engine absent the acoustic source.

6. A system as recited in claim 1, wherein the acoustic source is disposed in an inlet section of the gas turbine engine or an exhaust section of the gas turbine engine or a combustion section of the gas turbine engine or a plurality of acoustic sources are disposed in some combination of the inlet section and the exhaust section and the combustion section.

7. A system as recited in claim 1, wherein the acoustic source is disposed in a wall adjacent to the space.

8. A system as recited in claim 1, wherein the acoustic source is a narrow beam acoustic source.

9. A system as recited in claim 1, wherein both the first acoustic path and the second acoustic path cross the space between an inner wall closest to the axial shaft and an outer wall farthest from the axial shaft.

10. A system as recited in claim 9, wherein the acoustic source and the first acoustic sensor and the second acoustic sensor are all in an outer wall of the space farthest from the axial shaft.

11. A system as recited in claim 1, wherein the space is in a turbine section of the gas turbine engine.

12. A system as recited in claim 1, wherein the processor is further configured to cause the speed and the temperature determined for the fluid flow in the space to be presented on a display or to cause a change of operation of the gas turbine engine based on the speed and the temperature determined for the fluid flow in the space or both.

13. A method comprising:
    mounting a plurality of acoustic sensors in a gas turbine engine wherein the sensors are mounted to detect acoustic signals in a space of fluid flow in the gas turbine engine without extending into the space, a first acoustic sensor of the plurality of acoustic sensors is displaced a first distance from a different second acoustic sensor of the plurality of acoustic sensors in a first direction parallel to a direction of fluid flow through the space;
    detecting a first acoustic signal at the first acoustic sensor and a second acoustic signal at the second acoustic sensor;
    determining on a processor a first travel time difference between the first acoustic sensor and the second acoustic sensor based on the first acoustic signal and the second acoustic signal;
    determining on a processor a velocity of fluid flow in the space based at least in part on the first travel time difference; and
    determining on a processor a temperature of fluid flow in the space based at least in part on either the first acoustic signal or the second acoustic signal or both,
mounting an acoustic source to introduce a known acoustic signal into the space without extending into the space, wherein:
    determining the first travel time difference further comprises determining a difference between a first travel time and a second travel time, further comprising determining the first travel time based on a time the known acoustic signal is introduced into the space and a time of peak correlation of the known signal at the first sensor, and determining the second travel time based on the time the known signal is introduced into the space and a time of peak correlation of the known signal at the second acoustic sensor; and
    determining the temperature in the space further comprises determining the temperature based on a sum of the first travel time and the second travel time and a sum of a first length of a first path from the acoustic source to the first acoustic sensor and a second length of a second path from the acoustic source to the second acoustic sensor,
        wherein based on the determined temperature and velocity of fluid flow, profiles of temperature and velocity, respectively, are generated and utilized by the processor to ensure the gas turbine engine is operating within specified ranges, and
    wherein when the gas turbine is not operating within the specified ranges, adjustments are made within the gas turbine to attain improved performance of the engine.

14. A method as recited in claim 13, wherein the acoustic source is a resonator stick that is caused to emit the known acoustic signal in response to an acoustic activation signal at the time the known signal is introduced.

15. A method as recited in claim 13, wherein the acoustic source is disposed in an inlet section of the gas turbine engine or an exhaust section of the gas turbine engine or a combustion section of the gas turbine engine or a plurality of acoustic sources are disposed in some combination of the inlet section and the exhaust section and the combustion section.

16. A method as recited in claim 13, wherein the acoustic source is disposed in a wall adjacent to the space.

17. A non-transitory computer-readable medium carrying one or more sequences of instructions, wherein execution of the one or more sequences of instructions by one or more processors causes the one or more processors to perform at least the steps of:
    obtaining a first acoustic signal detected at a first acoustic sensor and a different second acoustic signal detected at a second acoustic sensor, wherein the sensors are mounted in a gas turbine engine to detect acoustic signals in a space of fluid flow in the gas turbine engine without extending into the space, and the first acoustic sensor is displaced a first distance from the second acoustic sensor in a first direction parallel to a direction of fluid flow through the space;
    determining a first travel time difference between the first acoustic sensor and the second acoustic sensor based on the first acoustic signal and the second acoustic signal;
    determining a velocity of fluid flow in the space based at least in part on the first travel time difference; and
    determining a temperature of fluid flow in the space based at least in part on either the first acoustic signal or the second acoustic signal or both;
mounting an acoustic source to introduce a known acoustic signal into the space without extending into the space, wherein:
    determining the first travel time difference further comprises determining a difference between a first travel time and a second travel time, further comprising determining the first travel time based on a time the known acoustic signal is introduced into the space and a time of peak correlation of the known signal at the first sensor, and determining the second travel time based on the time the known signal is introduced into the space and a time of peak correlation of the known signal at the second acoustic sensor; and
    determining the temperature in the space further comprises determining the temperature based on a sum of the first travel time and the second travel time and a sum of a first length of a first path from the acoustic source to the first acoustic sensor and a second length of a second path from the acoustic source to the second acoustic sensor;
        wherein based on the determined temperature and velocity of fluid flow, profiles of temperature and velocity, respectively, are generated and utilized by the processor to ensure the gas turbine engine is operating within specified ranges, and
    wherein when the gas turbine is not operating within the specified ranges, adjustments are made within the gas turbine to attain improved performance of the engine.

* * * * *